United States Patent
Fenn et al.

(10) Patent No.: US 6,690,976 B2
(45) Date of Patent: Feb. 10, 2004

(54) THERMOTHERAPY METHOD FOR TREATMENT AND PREVENTION OF BREAST CANCER AND CANCER IN OTHER ORGANS

(75) Inventors: Alan J. Fenn, Wayland, MA (US); John Mon, Silver Springs, MD (US)

(73) Assignee: Celsion Corporation, Columbia, MD (US)

( * ) Notice: Subject to any disclaimer, the term of this patent is extended or adjusted under 35 U.S.C. 154(b) by 0 days.

(21) Appl. No.: 10/193,110

(22) Filed: Jul. 12, 2002

(65) Prior Publication Data

US 2002/0193849 A1 Dec. 19, 2002

Related U.S. Application Data

(63) Continuation-in-part of application No. 09/548,630, filed on Apr. 13, 2000.

(51) Int. Cl.$^7$ ................................................. A61F 2/00
(52) U.S. Cl. ......................... 607/101; 607/102; 607/98
(58) Field of Search ...................... 607/96, 98, 99–102, 607/108–114; 606/2, 4, 9, 10–13, 32–34, 41–42; 601/2–3

(56) References Cited

U.S. PATENT DOCUMENTS

| | | | |
|---|---|---|---|
| 3,895,639 A | | 7/1975 | Rodler |
| 4,397,313 A | * | 8/1983 | Vaguine ...................... 607/104 |
| 4,397,314 A | | 8/1983 | Vaguine |
| 4,556,070 A | | 12/1985 | Vaguine et al. |
| 4,589,423 A | | 5/1986 | Turner |
| 4,633,875 A | | 1/1987 | Turner |
| 4,702,262 A | | 10/1987 | Andersen et al. |
| 4,798,215 A | | 1/1989 | Turner |
| 5,251,645 A | | 10/1993 | Fenn |
| 5,441,532 A | | 8/1995 | Fenn |
| 5,540,737 A | | 7/1996 | Fenn |
| 5,601,526 A | * | 2/1997 | Chapelon et al. ............... 601/3 |
| 5,810,888 A | | 9/1998 | Fenn |
| 6,126,619 A | * | 10/2000 | Peterson et al. ................ 601/2 |
| 6,163,726 A | | 12/2000 | Wolf |
| 6,200,598 B1 | | 3/2001 | Needham |
| 6,350,276 B1 | * | 2/2002 | Knowlton .................... 607/104 |
| 6,391,026 B1 | * | 5/2002 | Hung et al. .................... 606/41 |
| 6,436,061 B1 | * | 8/2002 | Costantino ..................... 601/2 |
| 6,613,350 B1 | * | 9/2003 | Zhang et al. ................. 424/449 |

FOREIGN PATENT DOCUMENTS

EP  0 519 415  12/1992

OTHER PUBLICATIONS

International Collaborative Hyperthermia Group, "Radiology With or Without Hyperthermia in the Treatment of Superficial Localized Breast Cancer: Results from Five Randomized Controlled Trials", Int J. Radiation Oncology Biol. Phys., vol. 35, No. 4, pp. 731–744, (1996).

(List continued on next page.)

Primary Examiner—Roy D. Gibson
(74) Attorney, Agent, or Firm—Venable LLP; Cathrine M. Voorhees

(57) ABSTRACT

A method for treating cancerous or benign conditions of an organ includes the steps of inserting an E-field probe sensor to a depth in the organ tissue, monitoring temperatures of the skin surface adjacent the organ, positioning two or more energy applicators around the organ, setting the initial relative phase delivered to each energy applicator to focus the energy at the E-field probe positioned in the organ tissue, delivering energy to the applicators to selectively irradiate the organ tissue, adjusting the power level to be delivered to each applicator during treatment based on the monitored skin temperatures, monitoring the energy delivered to the applicators, determining total energy delivered to the applicators and displaying the total energy in real time during the treatment, and completing the treatment when the desired total energy dose has been delivered by the energy applicators to the organ. Either focused or non-focused may be employed.

25 Claims, 16 Drawing Sheets

OTHER PUBLICATIONS

J. van der Zee, et al., "Results of Additional Hyperthermia In Inoperable Pelvic Tumors, Int. Congress on Hyperthermic Oncology", Rome, Italy, pp. 215–217, (1996).

Jay R. Harris, M.D., et al., "Breast Cancer", New England Journal Of Medicine, vol. 327, pp. 390–398, (1992).

Stuart J. Schnitt, M.D., et al., "The Relationship Between Microscopic Margins of Resection and the Risk of Local Recurrence in Patients With Breast Cancer Treated With Breast–Conserving Surgery and Radiation Therapy", vol. 74(6):1746–1751, (1994).

David P. Winchester, M.D., "Standards for Breast–Conservation Treatement", CA–A Cancer Journal for Clinicians, vol. 42(3):134–162, (1992).

Charles R. Smart, M.D., et al., "Twenty–Year Follow–Up of the Breast Cancers Diagnosed During the Breast Cancer Detection Demonstration Project", CA–A Cancer Journal for Clinicians, vol. 47, pp. 134–149, (1997).

Riccardo Valdagni, M.D., "Report of Long–Term Follow–Up In a Randomized Trial Comparing Radiation Therapy and Radiation Therapy Plus Hyperthermia To Metastatic Lymphnodes in Stage IV Head and Neck Patients", I.J. Radiation Oncology Biology Physics, vol. 28(1):163–169, (1994).

J. Overgaard, et al., "Hyperthermia as an Adjuvant to Radiation Therapy of Recurrent or Metastatic Malignant Melanoma", Int. J. Hyperthermia, vol. 12(1):3–20, (1996).

Eric J. Hall, "Radiobiology For The Radiologist", J.B. Lippincott Company, Fourth Edition, pp. 262–263, (1994).

Carlos A. Perez, et al., "Principles and Practice of Radiation Oncology, Hyperthermia", J.B. Lippincott Company, Second Edition, pp. 396–397, (1992).

Stephen A. Sapareto, Ph.D., et al., "Thermal Dose Determination in Cancer Therapy", A.J. Radiation Oncology Biology Physics., vol. 10, pp. 787–800, (1984).

Arthur R. von Hippel, et al., "Dielectric Analysis of Biomaterials", National Technical Information Service, U.S. Department of Commerce, DD Form 1473, pp. 1a–1c. (1973).

A. von Hippel, A.H. Runck et al., "Dielectric Analysis of Biomaterials", Massachusetts Institute of Technology, pp. i–ii and 1–20, (1973).

Merrill I. Skolnik, "Introduction to Radar Systems", McGraw–Hill, Inc., pp. 332–333, (1980).

R.T. Compton, Jr., "Adaptive Antennas Concepts and Performance", Prentice–Hall, Inc., p. 1, (1988).

Alan J. Fenn, "Evaluation of Adaptive Phased Array Antenna Far–Field Nulling Performance in the Near–Field Region", IEEE Transactions on Antennas and Propagation, vol. 38(2):173–185, (1990).

H. Bassen, et al., "Evaluation of an Implantable Electric–Field Probe Within Finite Simulated Tissues", American Geophysical Union, vol. 12(6(s)):25, (1977).

Alan J. Fenn, et al., "Adaptive Radiofrequency Hyperthermia–Phased Array System for Improved Cancer Therapy: Phantom Target Measurements", Int. J. Hyperthermia, vol. 10(2):189–208, (1994).

Alan J. Fenn, et al., "Improved Localization of Energy Deposition in Adaptive Phased–Array Hyperthermia Treatment of Cancer", The Journal of Oncology Management, pp. 22–29, (1998).

Alan J. Fenn, Ph.D., "Adaptive Focusing Experiments With An Air–Coled 915–MHz Hyperthermia Phased Array For Deep Heating of Breast Carcinomas", Massachusetts Institute of Technology, Surgical Application of Energy Sources, pp. 1–4, (1996).

Alan J. Fenn, et al., "An Adaptive Microwave Phased Array for Targeted Heating of Deep Tumors in Intact Breast: Animal Study Results", Int. J. Hyperthermia, vol. 15(1):45–61, (1999).

L. R. Gavrilov, et al., "Pre–Clinical Evaluation of a Two–Channel Microwave Hyperthermia System With Adaptive Phase Controlling a Large Animal", Int. J. Hyperthermia, vol. 15(6):495–507, (1999).

G. M. Samaras, et al., "Production of Controlled Hyperthermia Fields for Cancer Therapy", Urban & Schwarzenberg, pp. 131–132, (1978).

A. Y. Cheung, et al., "Dual–Beam TEM Applicator for Direct–Contact Heating of Dielectrically Encapsulated Malignant Mouse Tumor", The American Geophysical Union, vol. 12(6(S)):81–85, (1997).

National Council on Radiation Protection and Measurements, "Mammography—A User's Guide", Report No. 85, p. 6, (1986).

Susan M. Love, M.D., et al., "Dr. Susan Love's Breast Book", Addison–Wesley Publishing Company, Inc., pp. 191–196, (1990).

S.S. Chaudhary, et al., "Dielectric Properties of Normal & Malignant Human Tissues at Radiowave & Microwave Frequencies", Indian Journal of Biochemistry & Biophysics, vol. 21, pp. 76–79, (1984).

William T. Joines, et al., "The Measured Electrical Properties of Normal and Malignant Human Tissues from 50 to 900 MHz", Med. Physics, vol. 4, pp. 547–550, (1994).

Andrzej J. Surowiec, et al., "Dielectric Properties of Breast Carcinoma and the Surrounding Tissue" IEEE Transactions On Biomedical Engineering, vol. 35(4):257–263, (1988).

A M. Campbell, et al., "Dielectric Properties of Female Human Breast Tissue Measured in Vitro at 3.2 GHz", Phys. in Med and Biol., vol. 37(1):193–210, (1992).

Everett C. Burdette, "Electromagnetic and Acoustic Properties of Tissues", AAPM Medical Physics Monographs No. 8, pp. 105, 130, (1982).

S. Gabriel, et al., "The Dielectric Properties of Biological Tissues; III. Parametric Models for the Dielectric Spectrum of Tissues", Phys. Med. Biol., vol. 41, pp. 2271–2293, (1996).

Lawrence Bassett, M.D., et al., "Stereotactic Core–Needle Biopsy of the Breast: A Report of the Joint Task Force of the American College of Radiology American College of Surgeons, and College of American Pathologists", CA Cancer Journal Clinicians, vol. 47, pp. 171–190, (1997).

Daniel C. Sullivan, M.D., et al., "Measurement of Force Applied During Mamography", Duke University, Department of Radiology, pp. 355–357, (1991).

Dr. Michel Gautherie, (Editor), "Methods of External Hyperthermic Heating", Springer–Verlag, New York, p. 33, (1990).

Alan J. Fenn, et al., "Minimally Invasive Monopole Phased Arrays for Hyperthermia Treatment of Breast Carcinomas: Design and Phantom Tests", Presented at the 1994 International Symposium on Electromagneitic Compatibility, pp. 566–569, (1994).

S.B. Field, et al., "An Introduction to the Practical Aspects of Clinical Hyperthermia", Taylor & Francis, pp. 263–290, (1990).

David Vitrogan, "Elements of Electric and Magnetic Circuits", Rinehart Press, pp. 31–33, (1971).

Allen Taflove, "Advances in Computation al Electrodynamics", Artech House, Norwood, Massachusetts, p. 642, (1998).

Duck, "Physical Properties Of Tissue", A Comprehensive Reference Book, Academic Press, Chapter 6, pp. 167–223, (1990).

Dr. Susan Love, "Breast Book", Third Edition, Persus Publishing, pp. 130–131, (2000).

Winchester et al., "The Diagnosis And Management Of Ductal Carcinoma In–Situ Of The Breast", CA–A Cancer Journal For Clinicians, vol. 50(3):184–200, (2000).

Fisher et al., "Effect Of Preoperative Chemotherapy On The Outcome Of Women With Operable Breast Cancer", Journal of Clinical Oncology, vol. 16(8):2672–2685, (1998).

Fisher et al., "Effect of Preoperative Chemotherapy on Local–Regional Disease In Women With Operable Breast Cancer: Findings From National Surgical Adjuvant Beast And Bowel Project B–18", Journal of Clinical Oncology, vol. 15(7):2483–2493, (1997).

Gardner et al., "Focused Microwave Phased Array Thermotherapy For Primary Breast Cancer", Annals of Surgical Oncology, vol. 9(4):326–332, (2000).

Morrow et al., "Tamoxifen For The Prevention Of Breast Cancer In The High–Risk Woman", Annals Of Surgical Oncology, vol. 7(1):67–71, (2000).

Fisher et al., "Tamoxifen For Prevention of Breast Cancer: Report Of The National Surgical Adjuvant Breast And Bowel Project P–1 Study", Journal of the National Cancer Institute, vol. 90(18):1371–1388, (1998).

Gairard et al., "Proteins And Ionic Components In Breast Cyst Fluids", Endocrinology of Cystic Breast Disease, A. Angeli, et al editors, Raven Press, New York, pp. 191–195, (1983).

Bradlow et al., "Cations In Breast Cyst Fluid", Endocrinology of Cystic Breast Disease, , A. Angeli, et al editors, Raven Press, New York, pp. 197–201, (1983).

Lagendijk et al, "Hyperthermia Dough: A Fat And Bone Equivalent Phantom To Test Microwave/Radiofrequency Hyperthermia Heating System", Phys. Med. Biol., vol. 30(7):709–712, (1985).

Gautherie, "Methods of External Hyperthermic Heating", Springer Verlag, pp. 11, 33, (1990).

Mammography—A User's Guide, National Council on Radiation Protection and Measurements, NCRP Report No. 85, Aug. 1, 1987, p. 7.

Falk et al., "Invited Review—Hyperthermia on Oncology", Int. J. Hyperthermia, vol. 17(1):1–18, (2001).

Cancer Facts & Figures 2001, American Cancer Society, Inc., Atlantic, Georgia, pp. 1–41, (2001).

* cited by examiner

THERMOTHERAPY METHOD FOR TREATMENT AND PREVENTION OF BREAST CANCER AND CANCER IN OTHER ORGANS

This application is a C.I.P. of U.S. patent application Ser. No. 09/548,630, filed Apr. 13, 2000.

BACKGROUND OF THE INVENTION

The present invention generally relates to a minimally invasive method for administering focused energy such as adaptive microwave phased array hyperthermia for treating ductal and glandular carcinomas and intraductal hyperplasia as well as benign lesions such as fibroadenomas and cysts in compressed breast tissue. In addition, the method according to the invention may be used to treat healthy tissue containing undetected microscopic pathologically altered cells of high-water content to prevent the occurrence of or the recurrence of cancerous, pre-cancerous or benign breast lesions.

In order to treat primary breast cancer with hyperthermia, it is necessary to heat large volumes of tissue such as a quadrant or more of the breast. It is well known that approximately 90% of all breast cancers originate within the lactiferous ductal tissues (milk ducts) with much of the remaining cancers originating in the glandular tissue lobules (milk sacks) (Harris et al., The New England Journal of Medicine, Vol. 327, pp. 390–398, 1992). Breast carcinomas often involve large regions of the breast for which current conservative treatments have a significant risk of local failure. Schnitt et al., Cancer, Vol. 74 (6) pp. 1746–1751, 1994. With early-stage breast cancer, known as T1 (0–2 cm) or T2 (2–5 cm) cancers, the entire breast is at risk and often is treated with breast-conservin surgery combined with full-breast irradiation to destroy any possible microscopic (not visible to the human eye without the aid of a microscope or mammography) cancer cells in the breast tissue (Winchester et al., CA-A Cancer Journal for Clinicians, Vol. 42, No. 3, pp. 134–162, 1992). The successful treatment of invasive ductal carcinomas with an extensive intraductal component (EIC) where the carcinomas have spread throughout the ducts is particularly difficult, since large portions of the breast must be treated. Over 800,000 breast needle biopsies of suspicious lesions are performed annually in the United States with approximately 180,000 cases of cancer detected, the rest being nonmalignant such as fibroadenomas and cysts.

The use of heat to treat breast carcinomas can be effective in a number of ways, and in most cases the heat treatment must be capable of reaching, simultaneously, widely separated areas within the breast. Heating large volumes of the breast can destroy many or all of the microscopic carcinoma cells in the breast, and reduce or prevent the recurrence of cancer —the same approach is used in radiation therapy where the entire breast is irradiated with x-rays to kill all the microscopic cancer cells. Heating the tumor and killing a large percentage or all of the tumor cells prior to lumpectomy may reduce the possibility of inadvertently seeding viable cancer cells during the lumpectomy procedure, thus reducing local recurrences of the breast. Sometimes, the affected breast contains two or more tumor masses distributed within the breast, known as multi-focal cancer, and again the heating field must reach widely separated regions of the breast. Locally advanced breast carcinomas (known as T3) (Smart et al., A Cancer Journal for Clinicians, Vol. 47, pp. 134–139, 1997) can be 5 cm or more in size and are often treated with mastectomy. Pre-operative hyperthermia treatment of locally advanced breast cancer may shrink the tumor sufficiently to allow a surgical lumpectomy procedure to be performed—similar to the way pre-operative chemotherapy is currently used. Pre-operative hyperthermia treatment of locally advanced breast cancer may destroy the tumor completely, eliminating the need of any surgery.

It is well known that microwave energy can preferentially heat high-water content tissues such as breast tumors and cysts, compared to the heating that occurs in low-water content tissue such as fatty breast tissue. Many clinical studies have established that hyperthermia (elevated temperature) induced by electromagnetic energy absorption in the microwave band, significantly enhances the effect of radiation therapy in the treatment of malignant tumors in the human body (Valdagni, et al., International Journal of Radiation Oncology Biology Physics, Vol. 28, pp. 163–169, 1993; Overgaard et al., International Journal of Hyperthermia, Vol. 12, No. 1, pp. 3–20, 1996; Vernon et al., International Journal of Radiation Oncology Biology Physics, Vol. 35, pp. 731–744, 1996; van der Zee et al, Proceedings of the 7$^{th}$ International Congress on Hyperthermic Oncology, Rome, Italy, April 9–13, Vol. 11, pp. 215–217, 1996; Falk and Issels, Hyperthermia in Oncology, International Journal of Hyperthermia, Vol. 17, No. 1, 2001, pp. 1–18.). Radio-resistant cells such as S-phase cells can be killed directly by elevated temperature (Hall, Radiobiology for the Radiologist, 4$^{th}$ Edition, JB Lippincott Company, Philadelphia, pp. 262–263, 1994; Perez and Brady, Principles and Practice of Radiation Oncology, Second Edition, JB Lippincott Company, Philadelphia, pp. 396–397, 1994). Hyperthermia treatments with microwave radiating devices are usually administered in several treatment sessions, in which the malignant tumor is heated to about 43° C. for about 60 minutes. It is known that the amount of time to kill tumor cells decreases by a factor of two for each degree increase in temperature above about 43° C. (Sapareto, et al., International Journal of Radiation Oncology Biology Physics, Vol. 10, pp. 787–800, 1984). Thus, a 60-minute treatment at 43° C. can be reduced to only about 15 minutes at 45° C., which is often referred to as an equivalent dose ($t_{43° C.}$ equivalent minutes). It has also been clinically established that thermotherapy enhances the effect of chemotherapy (Falk and Issels, 2001). During treatments with noninvasive microwave applicators, it has proven difficult to heat semi-deep tumors adequately while preventing surrounding superficial healthy tissues from incurring pain or damage due to undesired hot spots. The specific absorption rate (SAR) in tissue is a common parameter used to characterize the heating of tissue. The SAR is proportional to the rise in temperature over a given time interval, and for microwave energy the SAR is also proportional to the electric field squared times the tissue electrical conductivity. The units of absolute SAR are watts per kilogram.

Non-coherent-array or non-adaptive phased array hyperthermia treatment systems typically can heat superficial tumors, but are restricted in their use for heating deep tumors or deep tissue, because they tend to overheat intervening superficial tissues, which can cause pain and/or burning. The first published report describing a non-adaptive phased array for deep tissue hyperthermia was a theoretical study (von Hippel, et al., Massachusetts Institute of Technology, Laboratory for Insulation Research, Technical Report 13, AD-769 843, pp. 16–19, 1973). U.S. Pat. No. 3,895,639 to Rodler describes two-channel and four-channel non-adaptive phased array hyperthermia circuits. Recent developments in hyperthermia systems effectively targets the delivery of heat to deep tissue using adaptive phased array technology originally developed for microwave radar systems (Skolnik, Introduction to Radar Systems, Second Edition, McGraw-Hill Book Company, 1980 pp. 332–333; Compton, Adaptive Antennas, Concepts and Performance, Prentice Hall, New Jersey, p. 1 1988; Fenn, IEEE Transactions on Antennas and Propagation, Vol. 38, number 2, pp. 173–185, 1990; U.S. Pat. Nos. 5,251,645; 5,441,532; 5,540,737; 5,810,888).

Bassen et al., Radio Science, Vol. 12, No. 6(5), November–December 1977, pp. 15–25, shows that an electric-field probe can be used to measure the electric-field pattern in tissue, and in particular, shows several examples in which the measured electric-field has a focal peak in the central tissue. This paper also discusses a concept for real-time measurements of the electric-field in living specimens. However, Bassen et al. did not develop the concept of measuring an electric-field using real-time with an electric-probe to adaptively focus a phased array.

An adaptive phased array hyperthermia system uses E-field feedback measurements to focus its microwave energy on deep tissue while simultaneously nullifying any energy that might overheat surrounding healthy body tissue. Pre-clinical studies indicate that adaptive microwave phased arrays have the potential for delivering deep heat while sparing superficial tissues from excessive temperatures in deep torso (Fenn, et al., International Journal of Hyperthermia, Vol. 10, No. 2, March-April, pp. 189–208, 1994; Fenn et al., The Journal of Oncology Management, Vol. 7, number 2, pp. 22–29, 1998) and in breast (Fenn, Proceedings of the Surgical Applications of Energy Sources Conference, 1996; Fenn et al., International Journal of Hyperthermia, Vol. 15, No. 1, pp. 45–61, 1999; Gavrilov et al., International Journal of Hyperthermia, Vol. 15, No. 6, pp. 495–507, 1999).

The most difficult aspect of implementing hyperthermia in deep breast tissues, with microwave energy, is producing sufficient heating at a predetermined depth while protecting the skin from burns. Noninvasive multiple applicator adaptive microwave phased arrays with invasive and noninvasive electric field probes can be used for producing an adaptively focused beam at the tumor position with adaptive nulls formed in healthy tissues as described in U.S. Pat. Nos. 5,251,645, 5,441,532, 5,540,737, and 5,810,888, all of which are incorporated herein by reference. Ideally, a focused microwave radiation beam is concentrated at the tumor with minimal energy delivered to surrounding healthy tissue. To control the microwave power during treatment, a temperature-sensing feedback probe (Samaras et al., Proceedings of the $2^{nd}$ International Symposium, Essen, Germany, Jun. 2–4, 1977, Urban & Schwarzenberg, Baltimore, 1978, pp. 131–133) is inserted into the tumor, however, it is often difficult to accurately place the probe in the tumor. An additional difficulty occurs in delivering hyperthermia to carcinoma spread throughout the ductal or glandular tissues of the breast, because of a lack of a well defined target position for the temperature-sensing feedback probe. In other situations, it is desirable simply to avoid inserting probes (either temperature or E-field) into the breast tissue in order to reduce the risk of infection or spreading the cancer cells when the probe passes through the tumor region.

The standard of medical care for treating benign cysts that have been detected varies from doing nothing to draining the cysts. The medically accepted position of not treating the cysts exists because the only known method of removing cysts involves invasive surgery. The alternative to surgically cutting and removing a cyst is draining the cyst. Draining the cyst is achieved by piercing the cyst and removing the liquid inside the cyst. While this method may temporarily relieve the pain associated with the cyst, the cyst may grow back if the draining procedure failed to remove the entire cyst. Therefore, there is a need for a non-invasive removal of these benign cysts.

The above shortcomings are solved by the Assignee of the instant invention's method for heating cancerous conditions of the breast which comprises the steps of inserting an E-field probe sensor in the breast, monitoring temperatures of the skin surface, orienting two microwave applicators on opposite sides of the breast, setting the initial microwave power and phase delivered to each microwave applicator in order to focus the field at the inserted E-field sensor, adjusting the microwave power to be delivered to the breast based on the monitored skin temperatures, and monitoring the microwave energy dose delivered to the breast being treated and completing the treatment when a desired total microwave energy dose has been delivered by the microwave applicators.

Moreover, the above method by the Assignee of the instant invention has application in situations such as when there is no well-defined position to place the temperature feedback sensor, or when it is desirable to avoid inserting a temperature probe into the breast tissue. Only a single minimally invasive E-field sensor is required in the preferred method taught by the Assignee. Thus, in the case of advanced breast cancer (e.g., a tumor 5–8 cm), this method can destroy a significant portion of the breast cancer cells and shrink the tumor or lesion (i.e., thermal downsizing to e.g., 2–3 cm) thereby replacing a surgical mastectomy with a surgical lumpectomy. In the alternative, the entire advanced breast cancer lesion can be destroyed and no surgery may be required. In early-stage breast cancer or for small breast lesions, the Assignee's method may destroy all of the breast cancer cells or benign lesions with heat (i.e., a thermal lumpectomy) thereby avoiding a surgical lumpectomy. In addition, the method can be used to enhance radiation therapy or for targeted drug delivery with thermosensitive liposomes as described in U.S. Pat. No. 5,810,888 and/or targeted gene therapy delivery. The assignee's method may be used with a recently developed temperature sensitive liposome formulation with chemotherapy agents such as doxorubicin as described in U.S. Pat. No. 6,200,598 "Temperature Sensitive Liposomal Formulation," Mar. 13, 2001 to Needham, in which drug agents are released at temperatures of approximately 39 to 45 degrees Celsius.

The assignee's method described above destroys the cancerous cells while sparing the normal glandular, ductal, connective, and fatty tissue of the breast. Thus, a thermal lumpectomy according to the invention avoids damage to such healthy tissue and is a breast conservation technique.

While the Assignee's method may be achieved employing the adaptive microwave phased array technology, focussing energy, in general, may be used to heat and ablate an area of tissue. The focused energy may include electromagnetic waves, ultrasound waves or waves at radio frequency. That is, any energy that can be focused to heat and ablate an area of tissue.

While the Assignee's method described above non-invasively removes cysts from breast tissue, other problems arise due to the externally focused microwaves and the mechanical pressure employed to compress the breast tissue. Thus, improvements in safety of such a non-invasive thermotherapy cancer treatment are needed.

SUMMARY OF THE INVENTION

Applicants overcome shortcomings in the prior art with their inventive method for treating cancerous or benign conditions of an organ by selective irradiation of the organ tissue with focused energy. The method according to the invention may include the steps of inserting an E-field probe sensor to an appropriate depth in the organ tissue, monitoring temperatures of the skin surface adjacent the organ, positioning two or more energy applicators around the organ, setting the initial power level delivered to each energy applicator, setting the initial relative phase delivered to each energy applicator to focus the energy at the E-field probe positioned in the organ tissue, delivering energy to the two or more energy applicators to selectively irradiate the organ tissue with focused energy and treat at least one of cancerous and benign conditions of the organ, adjusting the level of power to be delivered to each energy applicator during treatment based on the monitored skin temperatures, monitoring the energy delivered to the energy applicators, determining total energy delivered to the energy applicators and displaying the total energy in real time during the treatment, and completing the treatment when the desired total energy dose has been delivered by the energy applicators to the organ. The preferred organ to be treated is the breast and in a preferred method the energy applicators may be positioned in a ring about the breast (or other organ).

According to the invention, a preferred method for treating cancerous or benign conditions of an organ by selective irradiation of the organ tissue with energy may include the steps of injecting a substance that enhances heating to an appropriate depth in the organ tissue, monitoring temperatures of the skin surface adjacent the organ, positioning at least one energy applicator about the organ, setting the initial power level delivered to each at least one energy applicator, delivering energy to the at least one energy applicator to selectively irradiate the organ tissue with energy and treat at least one of cancerous and benign conditions of the organ, adjusting the level of power to be delivered to each at least one energy applicator during treatment based on the monitored skin temperatures, monitoring the energy delivered to the at least one energy applicator, determining total energy delivered to the at least one energy applicator and displaying the total energy in real time during the treatment, and completing the treatment when the desired total energy dose has been delivered by the at least one energy applicator to the organ. That is, Applicants envision that the method according to the invention may be achieved with a single applicator and may be any energy that can be focussed on the cancerous or benign conditions of the organ.

In accordance with the invention, microwave absorbing pads and metallic shielding are attached to microwave thermotherapy applicators and to the breast compression paddles. These safety precautions added to the Assignee's method reduce the electric-field intensity and temperature outside the primary microwave applicator aperture field in the vicinity of the base of the breast, chest wall region, and head and eyes during adaptive phased array thermotherapy in compressed breast tissue for breast tumor (malignant or benign) treatment.

In order to minimize the amount of invasive skin entry points, combined E-field and temperature sensors within a single catheter are used with the Assignee's method. As a result, only a single minimally invasive skin entry point is required resulting in improved patient comfort and reducing the risk of infection.

Additionally, adaptive microwave phased array thermotherapy can be used as a heat-alone treatment for early-stage breast cancer. Or adaptive microwave phased array thermotherapy can be used in combination with a chemotherapy regimen and/or gene based modifiers for treatment of the primary breast tumor in locally advanced breast cancer. Alternatively, the breast thermotherapy heat-alone treatment can be used as a pre-surgical tool to reduce the rate of second or third incisions (additional surgery) for lumpectomy patients. An additional use of adaptive microwave thermotherapy can be in improved breast cancer prevention in which thermotherapy is used with Tamoxifen or other anti-estrogen drug for blocking estrogen from binding to the estrogen receptors of breast carcinomas and for direct cancer cell kill by heat.

Further objectives and advantages will become apparent from a consideration of the description and drawings.

BRIEF DESCRIPTION OF THE DRAWINGS

The invention is better understood by reading the following detailed description with reference to the accompanying figures, in which like reference numerals refer to like elements throughout, and in which.

DETAILED DESCRIPTION OF THE PREFERRED EMBODIMENT

Dielectric Properties of Breast Tissue

Figure 1:
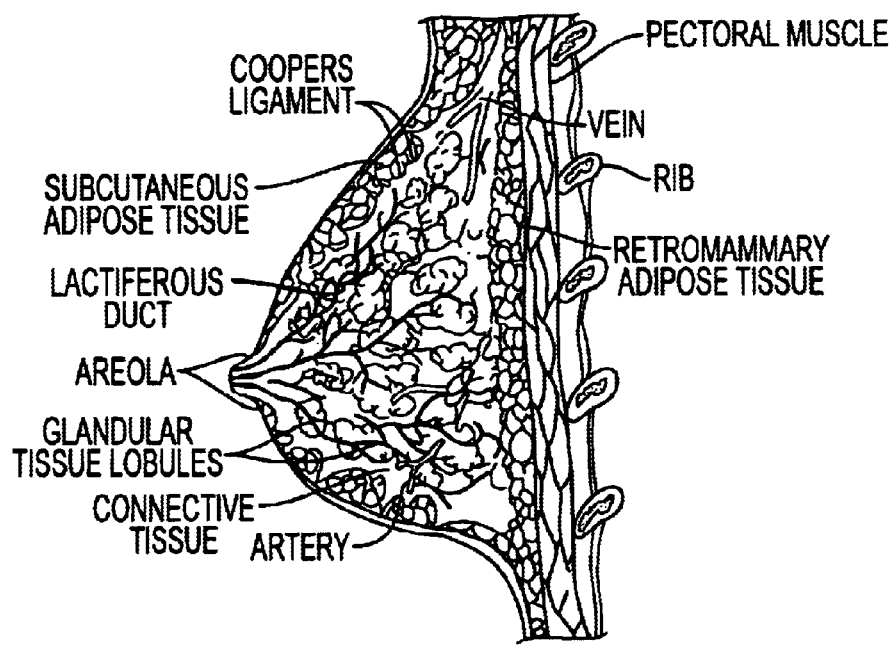
FIG. 1 is a detailed lateral view of the female breast.
Figure 2:
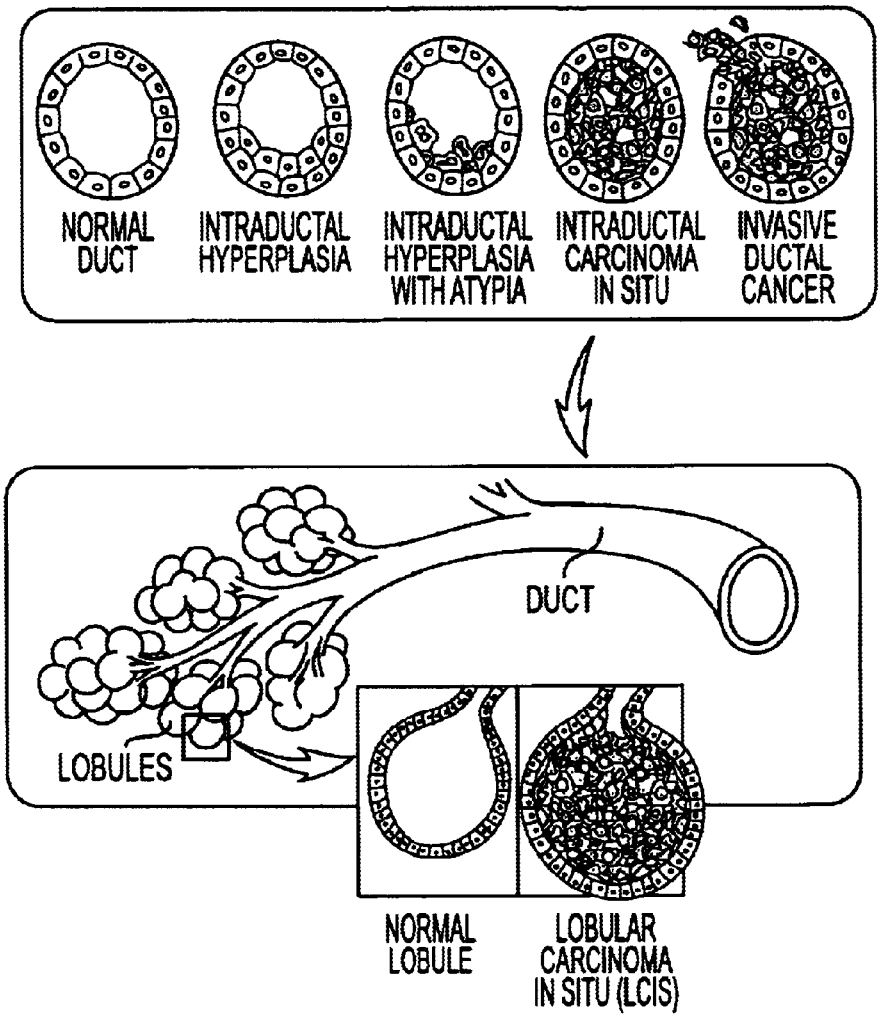
FIG. 2 shows examples of the progression of ductal carcinomas and lobular carcinomas in the ductal and glandular tissues of the breast.

A detailed lateral view of the female breast is shown in FIG. 1 (Mammography—A User's Guide, National Council on Radiation Protection and Measurements, NCRP Report No. 85, 1 August 1987, p.6). The amount of glandular and fatty tissue within the breast can vary widely, from primarily fatty tissue to extremely dense glandular tissue. Breast cancer cells, which are high-water content cells, usually form within the lactiferous ducts and glandular tissue lobules as depicted in FIG. 2 (adapted from Dr. Susan Love's Breast Book, Addison Wesley, Mass., 1990, pp. 191–196). The first indication of abnormal cell growth within the duct is referred to as intraductal hyperplasia, followed by intraductal hyperplasia with atipia. When the ducts become nearly full, the condition is known as intraductal carcinoma in situ (DCIS). These three conditions are referred to as pre-cancers. Finally, when the ductal carcinomas break through the ductal wall, the lesion is referred to as invasive ductal cancer. Cancer forms in the same way in the glandular lobules of the breast. All of the above cells are often cited as being high-water content with the exception of pure fat tissue (low-water content) and pure glandular/connective tissue (low to medium-water content) within the breast.

Figure 3:
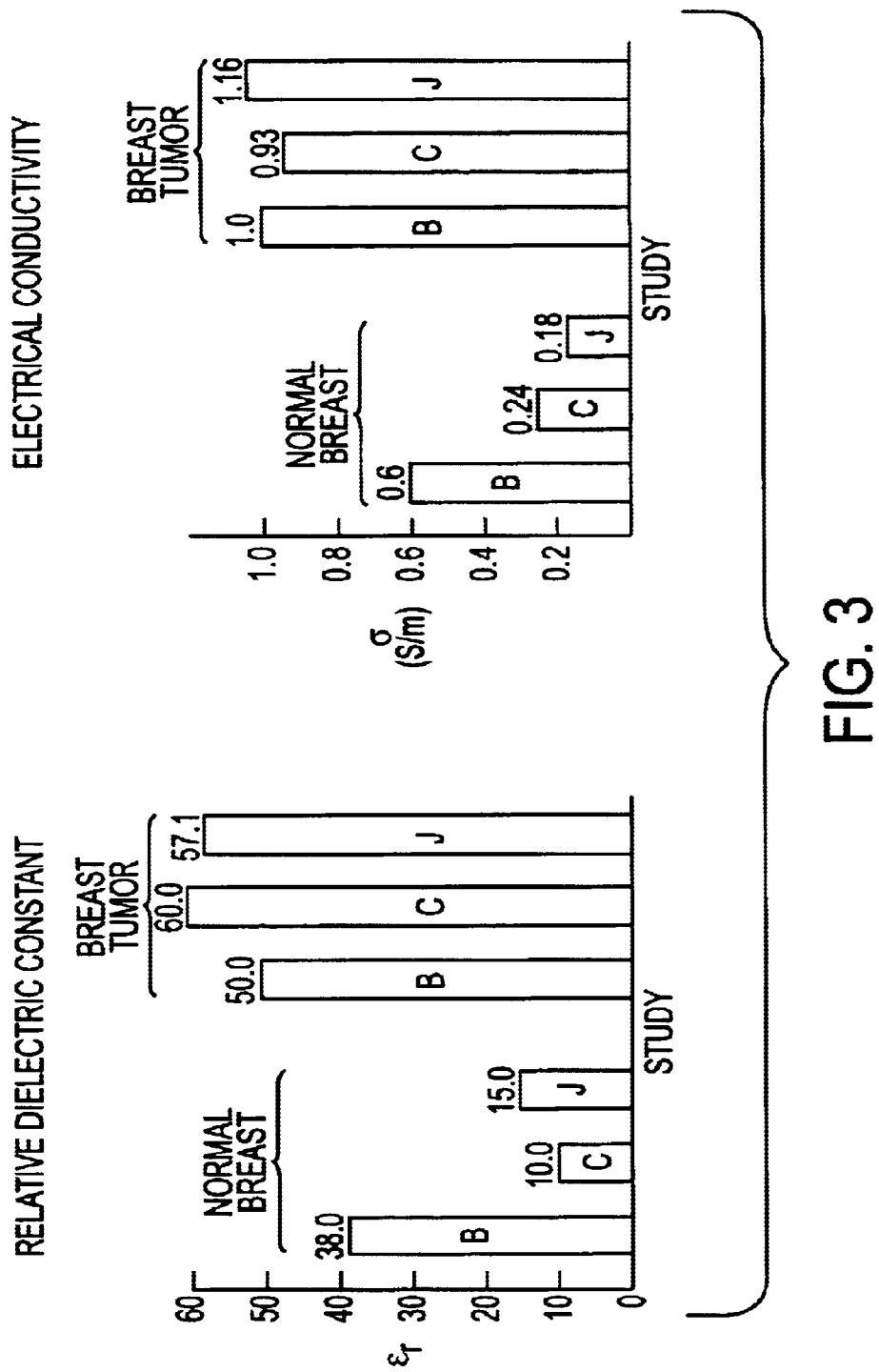
FIG. 3 shows the measured values of dielectric constant and electrical conductivity for normal breast tissue and breast tumor for three different studies. The study labeled B (Burdette) was for measurements through the breast skin which accounts for the differences between the other studies, denoted C and J.

Microwave radiation in the Industrial, Scientific, Medical (ISM) band 902 to 928 MHz is commonly used in commercial clinical hyperthermia systems, and is the primary frequency band considered here. Very little detailed microwave heating information on female breast tissues exists —however, it is well known that carcinomas of the breast are selectively heated compared to surrounding fatty breast tissues. Four main articles are: 1) Chaudhary et al., Indian Journal of Biochemistry and Biophysics, Vol. 21, pp. 76–79, 1984; 2) Joines et al., Medical Physics, Vol. 21, No. 4, pp. 547–550, 1994; 3) Surowiec et al., IEEE Transactions on Biomedical Engineering, Vol. 35, No. 4, pp. 257–263, 1988 and 4) Campbell and Land, Physics in Medicine and Biology, Vol. 37, No. 1, 193–210, 1992. Another article, Burdette, AAPM Medical Physics Monographs, No. 8, pp. 105, 130, 1982, has measured data for breast tissue, however, these data were measured through the skin and probably are not representative of breast tissue itself. The dielectric properties are usually given in terms of dielectric constant and electrical conductivity as depicted for normal breast tissue and breast tumor as shown in FIG. 3. At 915 MHz, removing the data from the Burdette study, the average dielectric constant of normal breast is 12.5 and the average conductivity is 0.21 S/m. In contrast, for breast tumor the average dielectric constant is 58.6 and the average conductivity is 1.03 S/m. Note: The data from Chaudhary et al (C) and Joines et al (J) studies are measured at room temperature (25° C). It should be noted that as temperature increases, generally the dielectric constant decreases and the electrical conductivity increases. The dielectric parameters of normal breast and breast tumor are similar to low-water content fatty tissue and high-water content muscle tissue, respectively. It should be noted that normal breast tissue contains a mixture of fat, glandular and connective tissues. Detailed information on 17 tissue types, including skin, muscle, and fat, is presented in an article by Gabriel et al, Phys. Med. Biol., Vol. 41, pp. 2271–2293, 1996. The article by Surowiec et al., has detailed information on selected glandular, ductal, fatty and cancerous tissues, but they only measured the parameters in the range 20 kHz to 100 MHz. It is possible to estimate the electrical properties of breast tissues at 915 MHz from data measured at 100 MHz. Applicants are not aware of any measured dielectric parameter data on pure ductal and glandular breast tissue for the frequency of interest, namely 915 MHz.

Figure 4:
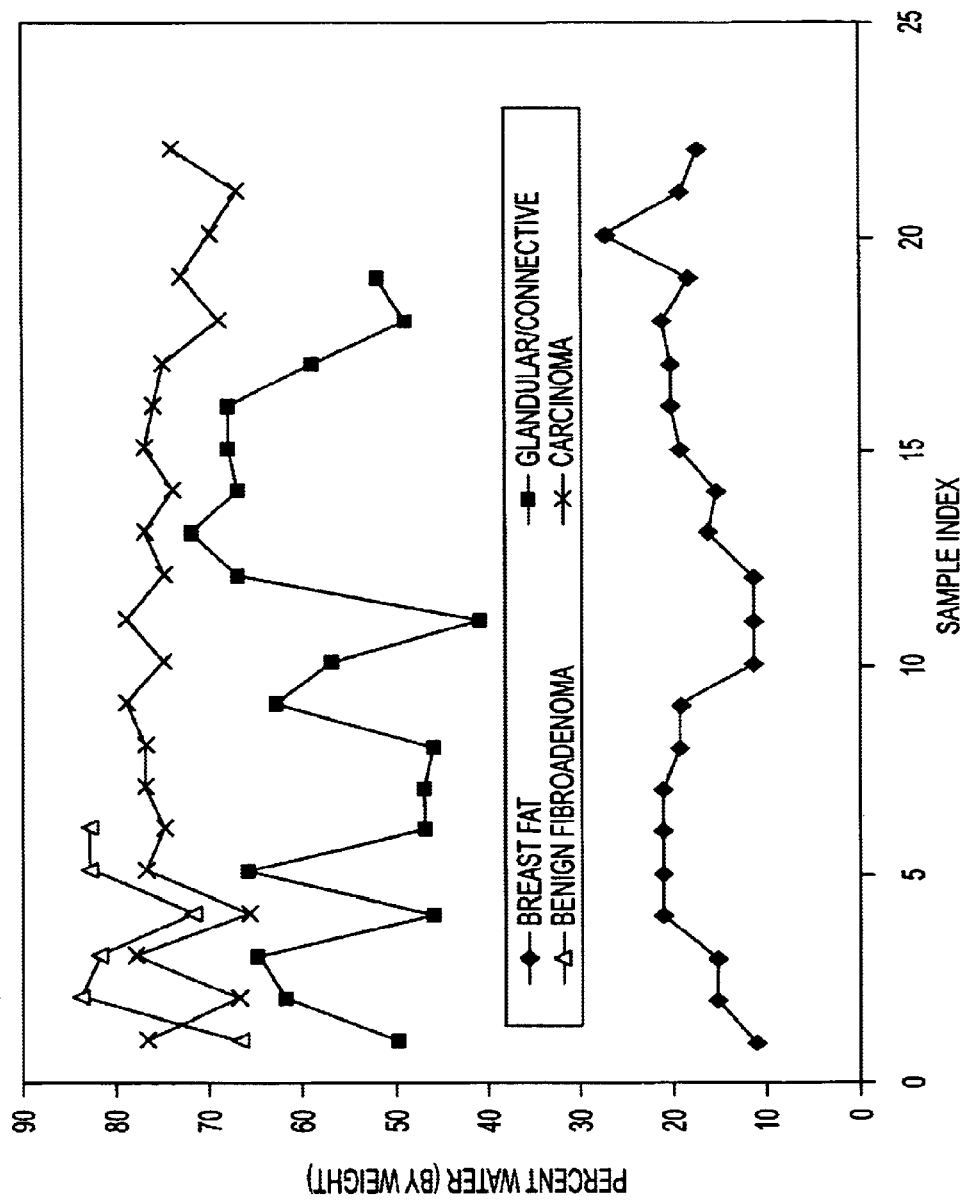
FIG. 4 shows the measured water content of breast fat, glandular/connective tissue, benign Fibroadenoma, and breast carcinoma (from Campbell and Land 1992)

The article by Campbell and Land has measured dielectric parameter data at 3.2 GHz, and the percent water content of breast fat, glandular and connective tissue, benign tumors (including fibroadenomas), and malignant tumors. Their measured data of percent water content can be used to assess the relative heatability of breast tissues, that is, higher water content tissues heat faster than lower water content tissues. The range of values for measured water content (by weight) is as follows: breast fat (11 to 31%), glandular and connective tissue (41 to 76%), benign tumors (62 to 84%), and malignant tumors (66 to 79%) where selected values are depicted in FIG. 4. Thus based on water content, it is expected that benign breast lesions and breast tumors will heat significantly faster than glandular, connective, and fatty breast tissues. Typically, for electrical conductivity at 3.2 GHz, their best choice of measured values is as follows: breast fat (0.11 to 0.14 S/m), glandular and connective tissue (0.35 to 1.05 S/m), benign tumors (1.0 to 4.0 S/m), and malignant tumors (3.0 to 4.0 S/m). Accordingly, the electrical conductivity of benign and malignant tumors tends to be up to about four times higher than the glandular and connective tissue and to about 30 times higher than pure fat. These data are consistent with the electrical conductivity data measured at 915 MHz by Chaudhary et al. as well as by Joines et al shown in FIG. 3.

Moreover, Chaudhary 1984 has measured electrical conductivity data for normal breast tissue at 3 GHz, where the conductivity is 0.36 S/m, consistent with the range (0.35 to 1.05 S/m) for normal glandular and connective tissue measured by Campbell and Land at 3.2 GHz. Thus, from the best available data, breast fat is low-water content, glandular and connective tissue is low to medium-water content, and breast tumors are high-water content. Accordingly, it is expected that benign and malignant tumor cells will be heated much more rapidly and to significantly higher temperatures than the surrounding fat, glandular, ductal, and connective tissue cells. In other words, only the microscopic and visible tumor cells are preferentially heated in this treatment, with all the surrounding fat, glandular, ductal, and connective tissues spared from heat damage.

Tissue electrical conductivity is a primary controlling parameter for tissue heating with microwave energy. Tissue electrical conductivity is also referred to as tissue ionic conductivity with units of Siemens per meter. Electrical conductivity is a function of the tissue properties primarily the water content, ion content, and temperature (F.A. Duck, Physical Properties of Tissue, Academic Press, 1990, Chapter 6, pp. 167–223). The electrical conductivity increases as the water content, ion content, and temperature of the tissue increases. For example, physiological saline has a higher ionic conductivity than pure water. Warm saline has a higher ionic conductivity than cool saline. Invasive or infiltrating breast cancer cells are reported as being moderately to poorly differentiated, meaning they increasingly lose the ability to function as normal cells. As cancer cells lose their functionality they can swell in size and absorb more water thereby increasing the percent water content. Ions in the water of a cancer cell play a significant role in the cell's ionic conductivity. Ions are electrically charged particles either positive or negative. The important ions in tissues include potassium (K+), calcium (Ca2+), sodium (Na+), and chlorine (Cl−). The calcium ion has two less electrons than protons and is positively charged (2+). Calcium can attract and hold two chlorine (Cl−) ions. Potassium can attract and hold only one chlorine (Cl−) ion. The calcium and chloride ions in calcium chloride (CaCl2) will dissociate or separate and increase in mobility when dissolved in water that increases the ionic conductivity of the water solution. Tightly clustered calcium deposits (known as microcalcifications) appearing on mammograms are often associated with carcinomas (S. M. Love, Dr. Susan Love's Breast Book, Third Edition, Persus Publishing, 2000, pp. 130–131). A tiny cluster of microcalcifications in a milk duct is usually attributed to precancer. Big chunks of calcium are usually associated with a benign lesion such as a fibroadenoma. Some of the calcifications appearing in the breast are from calcium leaving the bone, traveling through the blood stream and randomly deposited within the breast.

The proteins and ionic components in breast cyst fluid have been measured (B. Gairard, et al, "Proteins and Ionic Components in Breast Cyst Fluids", in Endocrinology of Cystic Breast Disease, A. Angeli, et al editors, Raven Press, New York, 1983, pp. 191–195. H. L. Bradlow, et al, "Cations in Breast Cyst Fluid," in Endocrinology of Cystic Breast Disease, A. Angeli, et al editors, Raven Press, New York, 1983, pp. 197–201.) Breast cyst fluids contain sodium (NA+), potassium (K+), chloride (Cl−), calcium (CA2+), phosphate (PO4−), and magnesium ions (Mg2+). Bradlow cites three categories of breast cyst fluids:

Type I: high levels of potassium (K+) and medium levels of sodium (Na+) and chloride (Cl−), Type II: high levels of potassium (K+) and sodium (Na+) and medium levels of chloride (Cl−), and Type III: high levels of sodium (Na+), medium levels of chloride (Cl−), and low levels of potassium (K+). The high-water and high-ion contents of breast cysts should allow preferential heating with microwaves when compared to the heating of surrounding normal healthy breast tissue.

There are several types of cysts: gross cysts forming palpable tumors, cysts containing inspissated (thickened) milk—so called "galactoceles", cysts evolving from duct ectasia, cysts resulting from fat necrosis, cysts associated with intraductal papilloma—so called "papillary cystadenoma, and cysts induced by the administration of estrogen. Gross (very large) cysts can develop quickly and obtain a moderate size that persists, while some decrease in size and even disappear with time. A considerable portion of gross cysts are discovered in the premenstrual or menstrual phase and enlarge rapidly and become painful and tender. Gross cysts are sometimes associated with signs of acute inflammation, pain, tenderness, and slight redness of the overlying skin. Following needle aspiration of the cyst fluid, signs of inflammation promptly subside. After aspiration is completed, only a fibrosed cyst wall remains. However, cyst fluid escaping into the surrounding breast tissue can produce acute irritation. Gross cysts are most common in the age group between 30 and 54 years, or about 95% of cases. The more extensively a surgeon operating for cystic conditions explores the breast, more cysts are likely to be found.

Fibroadenomas (very common benign lumps, also called fibroids) are smooth and hard and can vary in size from 5 mm up to about 5 cm. Fibroadenomas have a high water content (mean 78.5%, n=6) based on a small sample of measurements (Campbell and Land, Dielectric Properties of Female Human Breast Tissue Measured in vitro at 3.2 GHz, Phys Med Biol 1992; vol. 37(1), pp. 193–210) and should be readily heated by microwave energy compared to surrounding healthy breast tissue. These benign lesions are usually distinct on mammography and ultrasound and can be surgically removed if desired. Some patients will have multiple fibroadenomas, and breast conserving surgery then becomes impractical. Limited data exist for the measured water content of other benign tumors from the study by Campbell and Land as given below.

Benign fibrosis tumors: The median water content for one patient (age 26) in the Campbell and Land study was 65.5%, suggestive of high-water content. Fibrosis refers to the formation of fibrous tissue that can occur as a reparative or reactive process. Fibrous breast disease is a special type of fibrosis that suppresses and obliterates both the acini of the lobules and the mammary ducts in a localized portion of the breast, and forms a palpable tumor. Fibrosis is abnormally firm (but not as hard as a carcinoma) and usually requires a local excision; however, the limits of the disease are often not well defined since the lesion shape is irregularly discoid rather than rounded like a cyst.

Benign fibroadrosis tumors: The median water content for one patient (age 27) in the Campbell and Land study was 73.5% suggestive of high-water content.

Benign epitheliosis (also known as papillomatosis) tumors: The median water content for one patient (age 40) in the Campbell and Land study was 61% suggestive of high-water content. Papillomatosis is a papillary proliferation of the ductal epithelium which partly fills up smaller ducts and to a degree distends them. Papillomatosis is usually microscopic and appears often with cystic disease, tumor adnosis, multiple papilloma, or some other tumor-forming lesion.

Benign adnosis tumors: The median water content for one patient (age 43) in the Campbell and Land study was 38%, suggestive of low-water content. Benign adnosis is a proliferation of the acini of the mammary lobules appearing both microscopically and as a definite tumor. These tumors (benign adnosis) may not heat significantly compared to surrounding normal breast tissue, but only one data sample was measured and may not be representative of other benign adnosis tumors.

In summary, benign lesions such as cysts, fibroadenomas, fibrosis, fibroadrosis, and epitheliosis (also known as papillomatosis) appear to be high-water and/or high-ionic content and should be readily heated by microwave energy. Benign adnosis lesions may not heat as rapidly as cysts having high-water and/or high-ionic content; however, it is unclear as the data, upon which this is based, is limited to a single patient.

In the case of advanced breast cancer (e.g., a tumor 5–8 cm), the Assignee's inventive method can destroy a significant portion of the breast cancer cells with heat alone or with heat in combination with chemotherapy. By shrinking the tumor or lesion (i.e., thermal downsizing to e.g., 2–3 cm) it may be possible to replace a surgical mastectomy with a surgical lumpectomy. Ideally, the entire advanced breast cancer lesion can be destroyed (that is, a thermal mastectomy or a thermochemo mastectomy) and no surgery may be required. As discussed below, early-stage breast cancer or small breast lesions may be destroyed with the Assignee's inventive method. That is, all of the breast cancer cells or benign lesions may be destroyed with heat (i.e., a thermal lumpectomy) thereby avoiding a surgical lumpectomy.

Thermotherapy may be used as a heat-alone treatment prior to an initial (or second or third) lumpectomy to reduce the need for re-excision (additional surgery), which occurs when positive margins (cancerous cells) are detected in a lumpectomy specimen. Around 30% of lumpectomy specimen have positive margins that require a second incision. Since the method according to the invention heats tissue from the outside in to the target area (in contrast to RF ablation, which heats from the inside out), the method according to the invention addresses the margins. Hence, the thermotherapy treatment according to the invention can be applied prior to surgery with the expectation that cancer cells in the margins are ablated. As a result, after the initial surgery (lumpectomy), the area around the excised tissue (margins) is tested and a reduction in the cancer in the margins is expected thereby avoiding the need for a second (or third) incision. The thermotherapy treatment according to the invention theoretically could be employed as a thermo-lumpectomy, which replaces the invasive lumpectomy surgical procedure. Thus, the amount of cancer in the breast may be significantly reduced or destroyed in its entirety by the thermotherapy treatment according to the invention.

It is further envisioned that the thermotherapy treatment according to the invention could be used in combination with gene based modifiers to benefit patients that have abnormal (mutant) genes in their tissue, such as BRCA1, BRCA2, or other genes. The presence of these abnormal genes has been shown as increasing the risk of that patient getting cancer, and thus the ablation of these genes should reduce the patient's risk of getting cancer. Either a heat-alone thermotherapy treatment or thermotherapy with chemotherapy and/or gene based modifiers combined with heat should reduce breast cancer recurrence by destroying any cancerous cells in the margins thereby providing tissue free of cancer, or to destroy or repair mutant genes responsible for cancer and other diseases. In addition, the method can be used in combination with thermosensitive liposomes as described in U.S. Pat. No. 5,810,888 and/or targeted gene therapy delivery for treating breast lesions to enhance radiation therapy and/or for targeted drug delivery to aid in the destruction of cancerous or abnormal cells in the margins. Breast cancer begins within the breast ducts and then invades outwards into surrounding breast tissues and subsequently spreads outside the breast via the lymphatic and vascular (blood) systems. Thus, a thermotherapy treatment alone or in combination with chemotherapy and/or gene based modifiers should reduce breast cancer recurrence within the breast or other organs by killing cancer cells or mutant genes within the lymphatic and vascular systems of the breast.

The heat-treatment therapy according to the invention could be used alone or in combination with chemotherapy and/or gene based modifiers to pretreat other organs, such as the prostate, liver, ovaries, etc., in which the presence of abnormal or mutant genes may lead to a higher occurrence of cancer. In addition, the use of heat-alone thermotherapy or thermotherapy with chemotherapy and/or gene based modifiers may be beneficial when there is a presence of atypical cells in an organ, as determined by ductal lavage or other diagnostic technologies.

Thermotherapy for Early -Stage Breast Cancer

In a small group of early-stage breast cancer patients, Phase II clinical thermotherapy treatments conducted with the Celsion Corporation Microfocus APA 1000 breast thermotherapy system have significantly reduced the percent of viable tumor cells on the order of 70 to 90% employing either one or two heat-alone treatments. In certain patients, heat-alone thermotherapy may completely destroy breast cancer cells prior to a scheduled lumpectomy thereby avoiding surgery and preventing local recurrence of breast cancer. In other patients, heat-alone thermotherapy may reduce the need for second or third lumpectomies by providing margins free of cancer cells. These heat-alone treatments produce equivalent thermal doses (relative to 43 degrees C) up to approximately 200 minutes with peak tumor temperatures of 48.3 degrees C and a microwave energy dose of 250 kilojoules. Additional thermotherapy treatments, higher equivalent thermal dose and higher breast tumor temperatures may be required to complete heat-alone ablation of breast carcinomas. Tumor temperatures in the range of 49 to 50 degrees C or up to 55 degrees C may be required for complete ablation of tumors with an equivalent thermal dose of 400 minutes and a microwave energy dose up to 500 kilojoules. With these significant thermal and microwave energy doses it may be necessary to provide additional safety methods for protecting the breast skin and adjacent healthy tissues such as the chest wall region from any heat damage.

Thermotherapy for Ductal Carcinoma in-situ (DCIS)

Ductal carcinoma in situ, also known as DCIS or intraductal carcinoma, represents a major therapeutic dilemma. Approximately 41,000 new cases of DCIS were expected to be diagnosed in the year 2001 according to Cancer Facts and Figures 2001, American Cancer Society, Inc., Atlanta, Ga. In addition, 192,200 new cases of invasive breast cancer were expected. Out of the expected 238,600 cases of new breast cancers diagnosed, 80.6% are invasive, 17% are DCIS, the rest (2.4%) are LCIS (lobular carcinoma in situ) (Cancer Facts and Figures 2001). A needle biopsy diagnosis of DCIS may underestimate the presence of the invasive disease due to a sampling error. As a result of the sampling error, an accurate diagnosis of the disease progress can be difficult to obtain. Studies report that 16% to 20% of patients with DCIS diagnosed by needle biopsy were subsequently diagnosed with invasive disease upon surgical excision (D. P. Winchester, J. M. Jeske, R. A. Goldschmidt, "The Diagnosis and Management of Ductal Carcinoma In-Situ of the Breast", CA Cancer J Clin 2000; 50: pp.184–200). Thus, surgical excision is currently a requirement for DCIS patients, in order to determine an appropriate treatment strategy. For example, after an initial diagnosis of DCIS with a subsequent determination of invasive cancer following lumpectomy and pathology, the lymph nodes (particularly the sentinel lymph node(s)) may need to be biopsied and treated. At that time, stage appropriate systemic therapy may also be required. The major goal of any pathologic evaluation of a DCIS patient is to determine the level of risk of subsequent invasion so that proper treatment is offered and possible over- or under-treatment is avoided.

Based on mammographic and pathologic evaluation of the DCIS disease, in some cases breast-conserving surgery can be accomplished with an acceptable cosmetic result. However, long-term follow-up of DCIS patients treated with complete surgical excision and radiation therapy shows that as many as 19% or more of DCIS patients experience a local recurrence, with up to 50% of these local recurrences being invasive. For DCIS patients treated only with lumpectomy, the recurrence rate can be as high as 26%.

To understand the impact on the survival rates associated with a local recurrence, consider the following: For DCIS patients that have negative margins after surgery and standard postoperative radiation therapy, at least 80% will achieve long-term local control. That is, with long-term follow-up, approximately 20% of the patients will experience local recurrences. Of that 20%, 10% will have non-invasive recurrence and 10% will have invasive recurrence. The patients with non-invasive recurrence will achieve virtually 100% local control and cure with mastectomy. The patients with invasive local recurrence will experience a 75% five-year survival rate with mastectomy; that is, 25% will not survive five years. Thus, for patients with DCIS managed with breast-conserving treatment, 10% of the patients will have a non-invasive recurrence at a later date and must then have a mastectomy. The other 10% that have an invasive recurrence must have mastectomy, and 25% of those patients will die within 5 years. Thus, about 2.5% of patients receiving breast-conserving treatment (lumpectomy and radiation) for DCIS will die within 5 years of local recurrence. Based on 41,000 DCIS cases per year, 2.5% of these patients represents 1,025 DCIS patients that will die within 5 years from invasive recurrence. Given these percentages, most patients will choose a breast-conserving approach; however, these patients will experience significant side effects from the radiation therapy portion of breast conservation. It should also be noted that radiation therapy is a costly procedure and time-consuming (20 to 30 fractionated treatments are usually required).

A novel approach to treating ductal carcinoma in-situ (DCIS) is the use of thermotherapy (one or two treatments) following lumpectomy to provide a recurrence rate equal to or less than the recurrence rate for radiotherapy following lumpectomy, with fewer side effects. The cost for thermotherapy is expected to be less than the cost of radiation therapy, thus resulting in savings to the overall health cost. Thermotherapy may also be given several times with conventional radiation therapy for increased effectiveness in destroying ductal carcinoma in-situ (DCIS).

Thermochemotherapy for Locally Advanced Breast Cancer in the Intact Breast

According to the invention, for advanced breast cancer, heat and chemotherapy could be used together to destroy and/or downsize the primary breast cancer thereby converting mastectomy candidate patients to a more conservative lumpectomy surgery. In certain situations, patients may require pre-operative chemotherapy as part of their breast cancer treatment regimen. This would entail four cycles or courses of chemotherapy administered in accordance with standard pre-operative and post-operative chemotherapy delivery as in NSABP B-18 (Fisher et al., 1997, J. Clinical Oncology, vol. 15(7), pages 2483–2493; and Fisher et al, 1998, J. Clinical Oncology, vol. 16(8), pages 2672–2685). Each cycle of Adriamycin (Doxorubicin) at 60 mg/m$^2$ and Cytoxan (Cyclophosphamide) at 600 mg/m$^2$ is administered every 21 days. Tumor size is measured via a clinical exam and ultrasound imaging at the beginning of each cycle of chemotherapy. According to one embodiment of the invention, a focused microwave phased array thermotherapy session can be administered on the same day as the administration of the first, second, and third course of pre-operative AC chemotherapy or within 36 hours of administration of AC chemotherapy. The remaining (fourth) cycle of AC chemotherapy would then be administered without thermotherapy prior to surgery in order to allow sufficient time for any skin related thermotherapy effects to resolve (for example, skin blisters). It is not until after the fourth cycle of chemotherapy is completed that a final assessment is made of the breast to determine whether a mastectomy or a more conservative breast surgery will be made. Other combination chemotherapy treatments, such as Doxorubicin and Docetaxel or FAC (5-Fluorouracil, Doxorubicin, and cyclophosphamide), for breast cancer could be combined with thermotherapy for neoadjuvant treatment of breast cancer. Applicants also envision that thermotherapy could be applied prior to chemotherapy to shrink the breast tumor before chemotherapy is infused.

It is known that pre-operative AC chemotherapy will cause approximately 80% of breast cancer tumors to have some shrinkage. Tumor shrinkage is usually seen after the first course of AC chemotherapy is completed and is typically observed by ultrasound imaging about 21 days after the first course of AC chemotherapy is completed. There is not enough data to prove that the combination of thermotherapy and AC chemotherapy will cause tumors to shrink as much as AC chemotherapy by itself. Thus, in another embodiment, to see significant shrinkage it may be desirable to administer at least one dose of chemotherapy prior to administering thermotherapy. If three thermotherapy courses are used, thermotherapy will be administered on the same day or within 36 hours of the administration of the second, third, and fourth course of pre-operative chemotherapy. If two thermotherapy courses are used, thermotherapy could be administered on the same day or within 36 hours of the administration of the second and third course, or third and fourth course of pre-operative chemotherapy, or second and fourth course of chemotherapy.

Following the delivery of chemotherapy, thermotherapy is applied so that tumor temperatures reach between approximately 43–46 degrees C, and tumors receive equivalent thermal doses of approximately 50 to 100 minutes per treatment, and microwave energy doses of approximately 100 to 300 kilojoules. At the end of the fourth and last course of chemotherapy, the decision is made, based on the same guidelines used when the patient was enrolled in the study (that is, size and location of tumor, size of breast, patient health, and patient age), whether the patient will receive a mastectomy or a partial mastectomy (lumpectomy) for breast conservation. Following the pre-operative thermochemotherapy regimen, the usual standard of care (including drugs and radiation) will be given to all patients. At the discretion of the physician, patients that are estrogen-receptor positive will receive Tamoxifen at 10 mg twice a day for 5 years, beginning on the day after their last dose of chemotherapy. In addition, radiation therapy to the breast tissues and lymph nodes will be given as part of the standard of care for eligible patients.

Thermotherapy for Benign Breast Lesions

Recent Phase II clinical thermotherapy treatments of malignant breast lesions conducted with the Celsion Corporation Microfocus APA 1000 breast thermotherapy system revealed significant damage to breast carcinomas and benign breast lesions (cysts) from heat alone treatments. Based on these clinical treatments, tumor temperatures in the range of approximately 47 to 50 degrees C or up to approximately 55 degrees C may be required for complete ablation of benign breast lesions. The above tumor temperatures together with an equivalent thermal dose of up to 360 minutes and microwave energy dose up to 400 kilojoules should ablate benign breast lesions. Since analgesics (Naproxen Sodium tablets 220 mg) are normally administered to patients suffering from the pain of benign breast lesions, one or more thermotherapy treatments would be given together with analgesics for pain reduction according to a preferred procedure according to the invention.

Thermotherapy and Drug Therapy for Primary Breast Cancer Prevention

The current standard of care for breast cancer prevention is either prophylactic mastectomy (surgical removal of the breasts) or Tamoxifen treatment. Tamoxifen (and other drugs like raloxifene) is an antiestrogen drug which has an affinity for estrogen receptors and prevents estrogen from binding to breast carcinomas. In the NSABP P-1 Breast Cancer Prevention Trial, 13,175 participants received either Tamoxifen (20 mg daily for 5 years) or placebo. Overall a 49% reduction in the risk of invasive breast carcinomas was observed in the Tamoxifen (trade name Nolvadex) group (Fisher B., et al. "Tamoxifen For Prevention of Breast Cancer: Report of the National Surgical Adjuvant Breast and Bowel Project P-1 Study", Journal of National Cancer Institute, Volume 90, pp.1371–88, 1998; Morrow M. and Jordan V. C., "Tamoxifen for the Prevention of Breast Cancer in High-risk Woman", Annals Surg Oncol, Volume 7(1), pp. 67–71, 2000). A novel hypothesis is that thermotherapy added to a Tamoxifen prevention treatment may further increase the reduction in the risk of invasive breast carcinomas by increasing the amount of blockage of estrogen to the estrogen receptors of breast carcinomas. The amount of blockage of estrogen may be achieved by damaging or modifying the estrogen receptors and/or by killing breast carcinomas directly with the heat. In such a hypothesized clinical trial, patients in the thermotherapy and Tamoxifen arm would receive the standard dose of Tamoxifen (20 mg per day for 5 years) and thermotherapy at regular intervals during the same 5-year period. As it is envisioned that patients in such a clinical trial would not have a well defined lesion, the target region would simply be the upper portion of the breast where approximately 70% of all breast cancers occur as measured from the nipple to the upper base of the breast (Mammography—A User's Guide, NCRP Report No. 85, National Council on Radiation Protection and Measurements, Bethesda, p. 7, 1987). For thermotherapy treatment targeting the upper portion of the breast, breast compression would be in the cranial-caudal (head-to-toe) position and the E-field focusing probe would be positioned approximately 0.5 to 1.5 cm toward the cranial side of the breast (as measured from the central breast depth). A microwave energy dose of approximately 180 kilojoules (100 Watts total for 30 minutes) would be administered to the breast in each of multiple treatments spaced at approximately one-year intervals during the administration of Tamoxifen. A control group for this hypothetical clinical trial would include patients receiving Tamoxifen treatment only. An initial microwave power for each of the two channels may be approximately 50 Watts, which has been verified to be a safe power level based on the treatment of approximately 35 breast cancer patients in Celsion Corporation's Phase I and Phase II adaptive phased array breast thermotherapy clinical studies. Skin temperature sensors may be monitored and the microwave power of the two channels would be adjusted in order to keep skin temperatures below about 41 degrees Celsius during the thermotherapy treatment.

In thermotherapy treatments according to the invention for one of early-stage breast cancer, locally advanced breast cancer, benign breast lesions and breast cancer prevention, it is preferred that skin temperatures remain below approximately 40 to 42° C. during treatment. However, as discussed above, tumor temperatures may be generated in the range of approximately 43 to 50° C. or higher.

During Phase I and II clinical testing of the Celsion Microfocus 1000 externally focused adaptive phased array microwave system, applicants noted that, in a few, cases, the skin tissue in the vicinity of base of the breast, near the chest wall, was heated more strongly than desired. In addition, it was also discovered that mechanical compression of the breast tissue sometimes caused a non-thermal blister at the edge of the compression plate where pressure is the strongest. Consequently, the instant invention provides improvements to the Assignee's adaptive phased array microwave system to alleviate and/or reduce these side effects.

Figure 5:
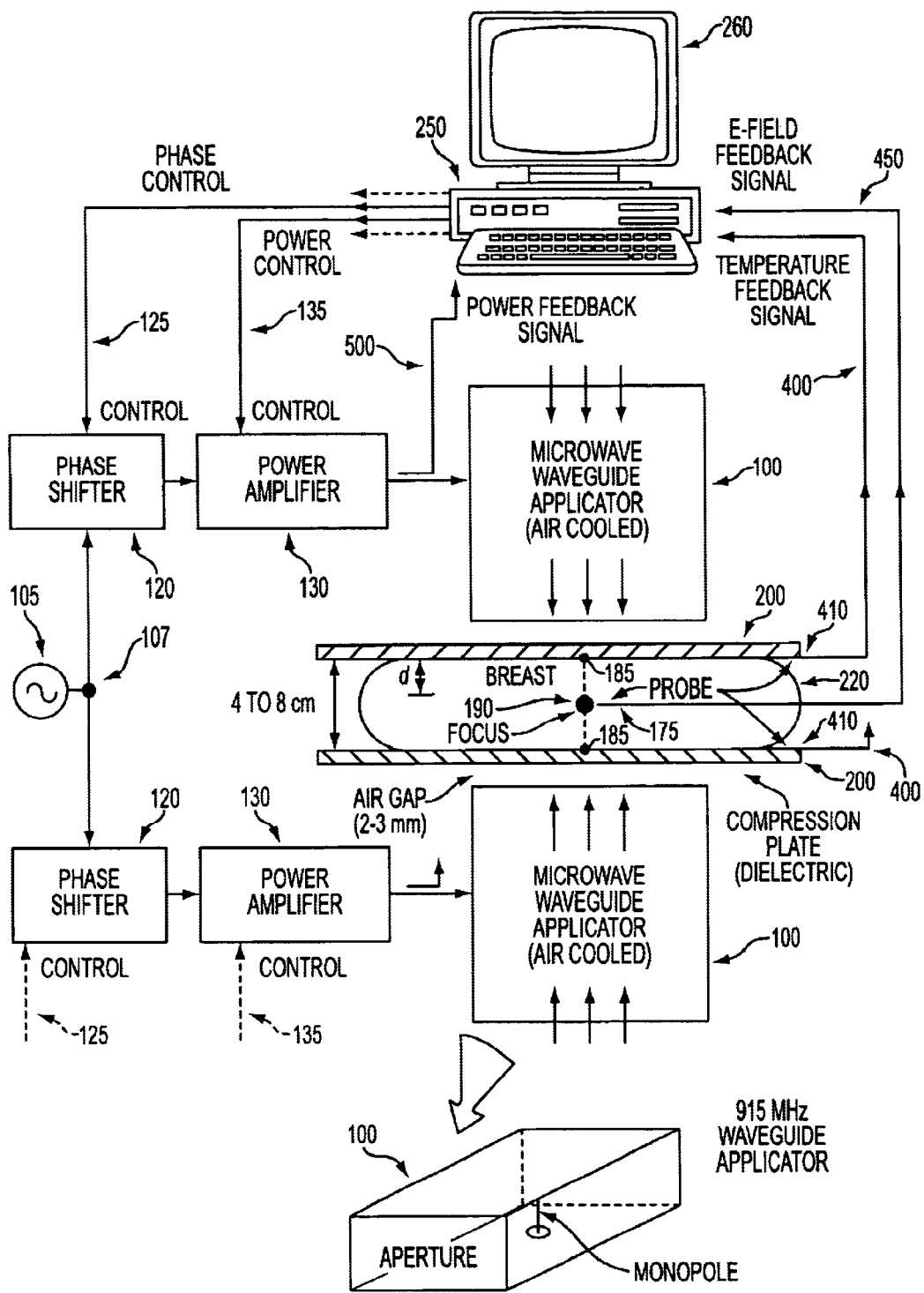
FIG. 5 shows the system according to the invention for heating the breast under compression.

Method for Heating Ductal and Glandular Carcinomas and Surrounding Breast Tissues FIG. 5 shows a preferred system for heating carcinomas in intact breast, using an adaptive microwave phased array hyperthermia system with E-field and temperature feedback. In order to heat deep tissues reliably at microwave frequencies, it is necessary to surround the body (breast) with two or more coherent applicators 100 controlled by an adaptive phased array algorithm. The black circle, indicated as focus 190, represents a tumor or healthy tissue that is to be treated. In the preferred embodiment, an E-field feedback probe 175 is used to focus the microwave radiation, and temperature feedback sensors 410 attached to the breast surface skin are used to adjust the microwave power level to heat the tumor to a desired temperature. A two-channel adaptive phased array is used to heat deep tissues within a compressed breast similar to the geometry used in x-ray mammography. Preferably, the E-field probe is used with an adaptive phased array fast-acceleration gradient search algorithm, as disclosed in U.S. Pat. No. 5,810,888 to Fenn, to target the microwave radiation at the tumor site.

Additionally, air-cooled waveguide applicator apertures preferably are used to provide a heating pattern that can heat large volumes of breast tissue containing ductal and glandular carcinomas. The air for cooling the waveguide apertures can be refrigerated, air-conditioned or room temperature. Based on the dielectric parameter differences at 915 MHz between high-water content tissues and fatty breast tissue, the high-water content ductal and glandular carcinoma tissues are expected to heat more rapidly than normal breast tissue. Thus, the treated region will be concentrated on the high-water content (cancerous and pre-cancerous) carcinoma tissue and benign lesions such as fibroadenomas and cysts, while sparing the normal (healthy) breast tissue.

The body or breast is compressed between two compression plates 200, which are made from a dielectric such as plexiglass that is transparent to microwaves. Breast compression has a number of potential advantages for intact breast hyperthermia treatments. Utilization of breast compression results in less penetration depth required to achieve deep microwave heating and reduces blood flow which also improves the ability to heat tissue. Compressing the breast to a flat surface improves the interface and electric-field coupling between the microwave applicator and the breast tissue, and allows a single pair of applicators to treat a wide range of breast sizes. Cooling of the breast compression plates with air during hyperthermia treatments helps avoid the potential for skin-surface hot spots. Compressing the breast with the patient in a prone position, such as that used in 20 to 40 minute stereotactic needle breast biopsy procedures (Bassett et al., A Cancer Journal for Clinicians, Vol. 47, pp. 171–190, 1997), maximizes the amount of breast tissue within the compression device. Mild compression immobilizes the breast tissue such that any potential patient motion complications are eliminated. The compression plates 200, which can include small apertures, are compatible with x-ray and ultrasound imaging techniques to accurately locate the central glandular/ductal region and assist in the placement of the invasive E-field probe sensor. The amount of compression can be varied from about 4 to 8 cm to accommodate patient tolerance during a 20 to 40 minute or longer hyperthermia treatment. A patient-comfort study of breast compression in mammography indicated that mammography was painful (defined as either very uncomfortable or intolerable) in only 8% of the 560 women examined. In that study the mean compression thickness was 4.63 cm with a standard deviation (1 sigma) of 1.28 cm (Sullivan et al., Radiology, Vol. 181, pp. 355–357, 1991). Thus, hyperthermia treatments under mild breast compression for 20 to 40 minutes or longer is feasible.

Prior to hyperthermia treatment, the breast is compressed between compression plates 200 and a single invasive E-field feedback sensor 175 is inserted within the central glandular/ductal/tumor tissue site (focus 190) in the breast, parallel to the polarization of the microwave applicators 100. E-field probe 175 is used in monitoring the focal E-field amplitude as the phase shifters are adjusted for maximum feedback signal using an adaptive phased array gradient search algorithm. Noninvasive temperature probes 410 are taped or otherwise secured to the skin surface of the breast to monitor the skin temperature. The temperature probes are typically oriented at right angles to the E-field polarization so as not to be heated by the microwave energy. The dual-applicator adaptive phased array of the invention together with the E-field feedback probe allows the phase shifters to be adjusted so that a concentrated E-field can be generated permitting focused heating in tissue at depth.

FIGS. 6 and 14 to 17 show an embodiment of safety methods applied to externally focused adaptive microwave phased array thermotherapy for treatment of breast tumors (malignant and benign).

Figure 6:
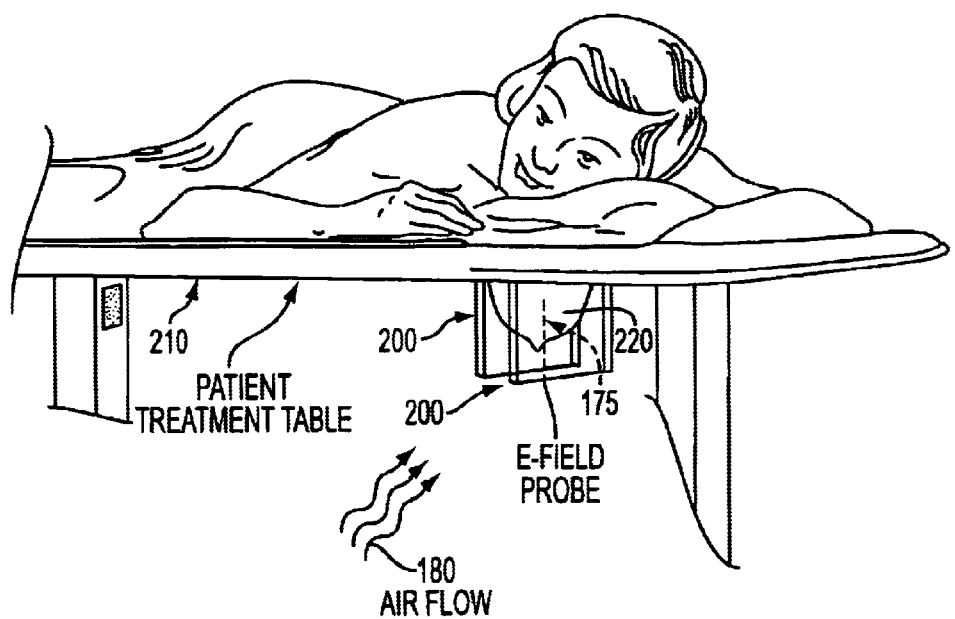
FIG. 6 shows the patient in a prone position with the breast compressed and an E-field probe inserted at the desired focal depth in the breast.

In a preferred method illustrated in FIG. 6, the patient lies prone with the breast pendulant through a hole in the treatment table 210 and the treated breast 220 is compressed with flat plastic compression plates 200, which immobilize the breast tissue, reduce blood flow, and reduce the penetration depth required for the microwave radiation. The treatment table 210 may be similar to a stereotactic imaging breast needle biopsy table such as manufactured by Fischer Imaging (Denver, Colo.) in which the table is metallic and covered by a soft pad for patient comfort. For breast imaging purposes, the metallic bed serves as a rigid structural support. For breast thermotherapy, the metallic table 210 also serves as a shield to microwave radiation so that the entire body, in particular the patient's head and eyes, are fully protected from any stray microwave radiation from the microwave applicators 100. The metallic table 210 can be fabricated from aluminum or steel or from plastic with either a metal foil or metal mesh coating. The table pad 212 can be a foam material and may contain microwave-absorbing material for additional shielding from stray microwave radiation from the applicators.

The breast compression plates are made of a microwave transparent plastic material, and may contain one or more apertures of rectangular or circular shape to allow imaging of breast tissues and placement of a minimally invasive E-field feedback probe 175 at the desired focal depth. Insertion of E-field feedback probe 175 may be achieved under the guidance of an ultrasound transducer. To provide additional protection against skin damage from the microwave fields, air flow 180 is provided by one or more cool-air fans (not shown).

As shown in FIG. 5, two or more temperature feedback probe sensors 410 are attached to the breast skin surface and produce the temperature feedback signals 400. Two microwave air-cooled waveguide applicators 100 are positioned on opposite sides of the compression plates 200. A 915 MHz microwave oscillator 105 is divided at node 107 and feeds phase shifters 120. The phase control signal 125 controls the phase of the microwave signal over the range of 0 to 360 electrical degrees. The microwave signal from phase shifter 120 feeds into the microwave power amplifier 130 which is controlled by a computer-generated control signal 135, which sets the initial microwave power level. Coherent 915 MHz microwave power is delivered to the two waveguide applicators 100 while phase shifters 120 in each channel are adjusted to maximize and focus the microwave energy at the E-field probe sensor 175 so that microwave power is maximized at the focus position 190. The treatment then begins.

During the hyperthermia treatment, the microwave power level delivered to each of the applicators 100 is measured as a feedback signal 500, and the power control is adjusted either manually or automatically to control the skin temperatures and equivalent thermal dose measured by the skin sensors 410 to avoid high temperatures that could cause skin burns or blisters. The amount of breast compression is adjusted by the compression plates 200 as necessary during treatment to provide patient comfort. Each time the breast compression is adjusted or the breast repositioned the phase shifters 120 are readjusted/refocused so that the E-field probe sensor 175 receives maximum power. The total microwave energy, since the start of the treatment, delivered to the microwave applicators is computed within the computer 250 and displayed on the computer monitor 260 during the treatment. The treatment is completed when a desired amount of total microwave energy is delivered to the microwave applicators 100. As an alternate embodiment, the total microwave energy calculated from the E-field feedback signal 450 received by the E-field probe 175 is used to control the length of the treatment. In order to determine the effectiveness of the treatment, the breast tissue is imaged with mammography means including x-ray and magnetic resonance imaging before and after the microwave total energy dose is administered, as well as pathological results from needle biopsy of the breast tissues.

As an alternate embodiment, the single invasive E-field probe 175 is replaced with two noninvasive E-field probes 185 positioned on the opposing skin surfaces. The total power measured by the two noninvasive E-field probes is minimized (as in U.S. Pat. No. 5,810,888) by adjusting the microwave phase shifters 120, creating a focused E-field probe in the central portion of the breast. With this embodiment, there is no risk of infection due to an inserted probe, there is no risk of scarring of the breast skin by the procedure of nicking the skin and inserting the probe, and any risk of spreading cancer cells by the probe passing through the tumor bed is avoided. Likewise, since both the temperature and E-field probes can be placed on the breast skin with this method embodiment, this method would work well when there is no defined single area.

Preferably, each channel (on either side of node 107) of the phased array contains an electronically-variable microwave power amplifier 130 (0 to 100 W), an electronically-variable phase shifter 120 (0 to 360 degrees), and air-cooled linearly-polarized rectangular waveguide applicators 100. Applicators 100 may be Model Number TEM-2 manufactured by Celsion Corporation, Columbia, Md. The rectangular aperture dimensions of a preferred pair of TEM-2 metallic waveguide applicators are 6.5 cm by 13.0 cm.

While the preferred embodiment discloses microwave energy at approximately 915 MHz, the frequency of the microwave energy may be between 100 MHz and 10 GHz. The frequency of the microwave energy could be selected from the range of 902 MHz and 928 MHz. In fact, lower frequencies of energy may be used to ablate or prevent cancerous tissue.

In a preferred embodiment, the initial microwave power delivered to each waveguide application is between 20 and 60 Watts. Over the entire treatment of the tissue, the microwave power delivered to each waveguide application may be adjusted over the range of 0–150 Watts to deliver the desired microwave energy dose and to avoid overheating the skin.

Dielectric loading of the side walls of the rectangular waveguide region of applicators 100 is used to obtain good impedance matching conditions for the TEM applicator microwave radiation (Cheung et al., "Dual-beam TEM applicator for direct-contact heating of dielectrically encapsulated malignant mouse tumor", Radio Science, Vol. 12, No. 6(S) Supplement, pp. 81–85, 1977; Gautherie (Editor), Methods of external hyperthermic heating, Springer-Verlag, New York, p. 33, 1990). The 1977 Cheung et al. article shows an example of dual-opposing non-coherent microwave applicators sequentially heating a mouse tumor—an E-field probe was not used in their experiments. Air cooling through the waveguide aperture is achieved by means of a fan (not shown) mounted behind a perforated conducting screen which serves as a parallel reflecting ground plane for the input monopole feed for the waveguide. Taking into account the thickness of the dielectric slabs in contact with the waveguide sidewalls, the effective cross-sectional size for the air-cooling is approximately 6.5 cm by 9.0 cm for the TEM-2 applicator. Based on the dielectric parameter differences at 915 MHz between high-water content tumor tissues and normal breast tissue, the high-water content ductal and glandular carcinomas and benign lesions are expected to heat more rapidly than normal breast tissue. Thus, the 50% SAR region will be concentrated on the high-water content (cancerous, pre-cancerous, and benign lesions including fibroadenomas and cysts) tissue while sparing the normal tissue.

In a preferred embodiment, a 0.9-mm outside-diameter (OD) invasive E-field coaxial monopole probe (semi-rigid RG-034), with the center conductor extended 1 cm, can be used to measure the amplitude of the electric field directed to the tissue and provide the feedback signal used to determine the necessary relative phase for the electronic phase shifters prior to treatment. Coaxially-fed monopole probes of this type have been used to make accurate measurements of linearly polarized electric fields in compressed breast phantoms (Fenn et al., International Symposium on Electromagnetic Compatibility May 17–19, 1994 pp. 566–569) Journal of Hyperthermia, Vol. 10, No. 2, March-April, pp. 189–208, 1994). This linearly-polarized E-field probe is inserted within a 1.5 mm OD teflon catheter. Thermocouple probes (Physitemp Instruments, Inc., Type T copper-constantan, enclosed within a 0.6 mm OD teflon catheter) were used to measure the local temperature in the tumor during treatment. These temperature probes have a response time of 100 ms with an accuracy of 0.1° C.

Compressed Living Breast Tissue Heating Tests

As part of an FDA-approved Phase I clinical study conducted by the Assignee, Celsion Corporation, beginning in December 1999, several volunteer patients, with breast tumors varying in maximum dimension from 3 to 6 cm, were treated with an adaptive microwave phased array where both E-field and temperature probes were inserted into the breast tissue. Patients received a 40-minute treatment of hyperthermia and approximately one-week later underwent mastectomy. This clinical study included a measurement of the power delivered to the microwave applicators, which was used to compute the delivered microwave energy dose, but was not used to control the duration of the treatment. More detailed information regarding this Phase I clinical study is published in Gardner et al, "Focused Microwave Phased Array Thermotherapy For Primary Breast Cancer," *Annals Surg Oncol*, Volume 9(4), pp. 326–332, May 6, 2002.

The E-field probe was used with the adaptive phased array fast-acceleration gradient search algorithm, as disclosed in U.S. Pat. No. 5,810,888 to Fenn, to target the microwave radiation at the tumor site. The temperature sensed by the invasive temperature probe in the tumor was used as a real-time feedback signal during the treatment. This feedback signal was used to control the microwave output power level of the variable power amplifiers, which set and maintained the focal temperature at the tumor site in the range of 43 to 46° C. The power and phase delivered to the two channels of the phased array were adjusted adaptively using digital-to-analog converters under computer control.

The breast compression plates were made of an acrylic material (plexiglass) which is a low-loss dielectric material and nearly transparent to microwave fields. The compression plates contained square cut-outs (apertures), approximately 5.5 cm on a side, which accommodate small ultra-sound transducers (nominally 4 cm in length) to assist in placement of the minimally invasive probes (E-field and temperature). The cut-outs also allow improved air flow to cool the skin.

Based upon the results from these recent microwave hyperthermia clinical tests with adaptive microwave phased array treatment, Applicants recognized, in living breast tissue compressed to 4.5 to 6.5 cm, that a microwave energy dose of between 138 kJ (kilojoules or equivalently kW seconds) and 192 kJ produces an equivalent thermal dose ranging from 24.5 minutes to 67.1 minutes relative to 43° C. as listed below in Table 1.

TABLE 1

Equivalent thermal dose (minutes) and total microwave energy (kilojoules) delivered in the four compressed living breast tissue tests.

| | $T_{43° C.}$ equivalent thermal dose measured in tumor (minutes) | Total Microwave Energy Dose (kJoules) |
|---|---|---|
| Test 1 | 41.0 | 192.0 |
| Test 2 | 24.5 | 162.0 |
| Test 3 | 67.1 | 186.0 |
| Test 4 | 47.8 | 138.0 |
| Average | 45.1 | 169.5 |

Thus, the Total Microwave Energy Dose can be used to estimate the required heating time. That is, Applicants realized that a non-invasive equivalent temperature sensing means could replace the invasive temperature probes, and that the Total Microwave Energy Dose reliably could be used to control the duration of treatment. In Table 1, the average thermal dose is 45.1 minutes and the average Total Microwave Energy is 169.5 kJ. In these four tests, the maximum energy value (192.0 kJ) varies by only 13% from the average and the minimum energy value (138.0 kJ) varies by only 14% from the average. The breast compression used in these tests, as mentioned earlier, reduces blood flow which likely eliminates the effects of blood flow on the required microwave energy for treatment, and may help explain the small variation in energy required in these tests. Applicants also recognized that post treatment imaging of these four tests typically showed significant damage to the tumor, but little or no damage to the skin, breast fat, and normal glandular, ductal, and connective tissues.

Accordingly to a preferred embodiment of the method, the total microwave energy delivered to the waveguide applicators to determine completion of the treatment is between 25 kilojoules and 250 kilojoules. The total amount of microwave energy dose that would destroy any cancerous or precancerous tissue would be approximately 175 kilojoules. But, under certain conditions, the required microwave energy dose may be as low as 25 kilojoules. In another embodiment according to the invention, higher microwave energy doses up to 400 kilojoules may be employed to completely destroy cancerous tumor cells.

Table 2 below lists the breast tissue compression thickness for the four tests. It should be noted that the smallest compression thickness (4.5 cm) corresponds to the smallest energy dose (138 kJ) delivered, with both occurring in Test 4. As applicants recognized and will be proven theoretically below, smaller compression thickness may require less microwave energy dose (compared to larger compression thickness) for effective treatments in preventing or destroying cancerous, pre-cancerous or benign lesions.

TABLE 2

Breast compression thickness for the four compressed living breast tissue tests.

|  | Breast Compression Thickness (cm) |
|---|---|
| Test 1 | 6.5 |
| Test 2 | 6.5 |
| Test 3 | 6 |
| Test 4 | 4.5 |

From these clinical studies, it becomes apparent that it is important to select an appropriate initial microwave power level ($P_1, P_2$) delivered to each applicator as well as the proper microwave phase between the two applicators to focus the energy at the area to be treated. From the compressed breast experiments, the following data was obtained for the four tests as listed in Table 3:

TABLE 3

Initial microwave power and initial microwave phase to focus the radiation in compressed living breast tissue.

|  | Initial Microwave Powers $P_1, P_2$ (W) | Relative Microwave Phase (deg) |
|---|---|---|
| Test 1 | 30 | −90 |
| Test 2 | 30 | −180 |
| Test 3 | 40 | −180 |
| Test 4 | 40 | −10 |

As can be seen from Tables 1 and 3, initial microwave power of 30 to 40 watts for each applicator was sufficient to achieve significant thermal doses. Further, the initial relative microwave phase between the applicators varied from −10 electrical degrees to −180 electrical degrees and does not follow any definite trend, proving that it is necessary to always focus the microwave radiation with an E-field sensor.

For comparable compression thickness, 6.5 and 6.0 cm in Tests 2 and 3, respectively, the microwave power level was held constant for the first few minutes of the treatments in order to determine the linear temperature rise in the tumor—this in effect provides a measurement of the SAR. It was found for 30 watts of power, that it took 2.5 minutes to achieve a one-degree C temperature rise in the tumor. For 40 watts of power, it took only 1.5 minutes to achieve a one-degree C temperature rise.

During hyperthermia treatment, it is necessary to monitor the skin temperatures so that they do not rise significantly above about 41 degrees Celsius for more than several minutes. The equivalent thermal dose for the skin can be calculated (Sapareto, et al., International Journal of Radiation Oncology Biology Physics, Vol. 10, pp. 787–800, 1984) and can be used as a feedback signal. Typically, it is necessary to avoid delivering more than a few equivalent minutes thermal dose. Avoiding high skin temperatures according to the invention is accomplished by adjusting the individual powers ($P_1$, $P_2$) delivered to the applicators during treatment either by manual or automatic computer control.

Applicants recognize that Doppler ultrasound can be used to measure blood flow in tumors and surrounding breast tissue, before and during treatment to plan and adjust the microwave energy dose. For example, less energy dose is required when the tumor blood flow rate is reduced which can occur when the breast is compressed and/or the tumor is heated to therapeutic temperatures. Alternatively, the water content and dielectric parameters of breast tumor tissue from needle biopsies could be measured and used to determine, prior to the treatment, the required microwave energy dose. For example, higher water content and higher electrical conductivity in the tumor would reduce the amount of required microwave energy dose. In addition to the above variables, the size of the tumor impacts the required microwave energy dose. Larger tumors are more difficult to heat than smaller tumors and require a larger microwave energy dose. An initial treatment planning session involving a low-dose delivery of microwave energy to assess the heatability of the tumor, followed by a complete treatment at the full required microwave energy dose may be performed.

Simplified Microwave Radiation Theory

Microwave energy from hyperthermia applicators, in the near field of a body, radiates as a spherical wave with the electric-field amplitude varying, in part, as the inverse of the radial distance r from the applicator. Additionally, the amplitude decays as an exponential function of the product of the attenuation constant $\alpha$ of the body tissue and the distance d traversed (or depth) within the body. The electric-field phase varies linearly with distance according to the product of the phase propagation constant $\beta$ and distance d. For simplicity, dual-opposing applicators are analyzed here under the assumption that the applicator radiation is approximated by a plane wave. Mathematically, the plane-wave electric field versus depth in tissue is given by $E(d) = E_o \exp(-\alpha d) \exp(-i\beta d)$, where $E_o$ is the surface electric field (in general represented by an amplitude and phase angle), i is the imaginary number (Field and Hand, An Introduction to the Practical Aspects of Clinical Hyperthermia, Taylor & Francis, New York p. 263, 1990).

Plane-wave electromagnetic energy, at the microwave frequency of 915 MHz, attenuates at a rate of about 3 dB per cm in high-water content tissue, such as ductal or glandular breast tumor, and about 1 dB per cm in normal breast tissue. Thus, a single radiating applicator has a significant fraction of its microwave energy absorbed by intervening superficial body tissue compared to the energy that irradiates deep tissue, likely creating a hot spot in superficial tissue. Since skin surface cooling with either air or water protects tissue only to a maximum depth of about 0.25 to 0.5 cm, in order to avoid hot spots, it is necessary to introduce a second phase-coherent applicator, having the same microwave radiation amplitude as the first applicator. The second phase-coherent applicator can theoretically increase the power (and hence the energy) delivered to deep tissue by a factor of four compared to a single applicator (Field and Hand, p. 290, 1990).

The phase characteristics of the electromagnetic radiation from two or more applicators (known as a phased array) can have a pronounced affect on the distribution of power delivered to different tissues. The relative specific absorption rate (SAR) in homogeneous tissue is approximated by the square of the electric-field amplitude $|E|^2$. The SAR is proportional to the rise in temperature over a given time interval. A simplified case, homogeneous breast tissue, in which the microwave radiation is focused at a central tissue site is described in detail below. As described in article by Fenn et al., International Symposium on Electromagnetic Compatibility, Sendai, Japan, Vol. 10, No. 2, May 17–19, 1994, pp. 566–569, 1994, the effects of multiple microwave signal reflections within the breast phantom can be ignored.

The wavelength in homogeneous normal breast tissue (with approximate dielectric constant 12.5 and electrical conductivity 0.21 S/m (values averaged from Chaudhary et al., 1984, Joines et al., 1994) is approximately 9.0 cm at 915 MHz, and the microwave loss is (1 dB/cm). The attenuation constant $\alpha$ is 0.11 radians/cm and the propagation constant $\beta$ is 0.69 radians/cm. (For a phantom thickness of 4.5 cm, the electric field of a single applicator radiating on the left side is $E_o$ at the surface, $-i0.8E_o$ (where i represents a 90-degree phase shift) at the central position (2.25 cm deep), and $-0.6E_o$ at the right surface. Combining two phase coherent applicators yields an electric-field value of $0.4E_o$ on both surfaces and $-i1.6E_o$ at the central position (2.25 cm depth). Thus, for breast that there is a significantly lower SAR at the surface, by a factor of 16 compared to the central SAR. The 180-degree phase shift experienced by the microwave field transmitted through 4.5 cm of breast tissue, partly cancels or nulls the field entering the tissue with 0-degree phase shift. Due to destructive interference of the microwaves away from the central focus lower temperatures in the superficial breast tissues would be expected. Measurement and enforcement of lower SAR on the opposing skin surfaces effectively focuses the microwave energy deep in the breast.

The adaptive phased array system according to the invention uses two microwave channels, fed by a common oscillator 105, containing two electronically adjustable phase shifters 120 to focus the microwave energy at an E-field feedback probe 175. This inventive adaptive phased array system has significant advantage over a non-adaptive phased array. A non-adaptive phased array with two channels could, in theory, produce a null, a maximum, or an intermediate value of E-field depending on whether the two waves are 180 degrees out-of-phase, completely in-phase, or partly out-of-phase, respectively. That is, the microwave phase delivered to the microwave applicators, according to the invention, can be adjusted between −180 degrees and 180 degrees before and during the treatment to create a focused field in the breast tissue.

Because the adaptive phased array according to the invention automatically focuses the E-field in the presence of all scattering structures in the tissue, this type of array should provide more reliable deep focused heating compared to manually adjusted or pre-treatment planning controlled phased arrays as described in U.S. Pat. No. 4,589,423 to Turner. Furthermore, the adaptive phased array system according to the preferred embodiment of the invention does not use an invasive metallic temperature probe which could scatter or alter the E-field at the tumor site.

Calculation of Microwave Energy

Electrical energy consumption is commonly expressed in units of kilowatt hours. Mathematically, the expression for the microwave energy W delivered by an applicator is given by (Vitrogan, Elements of Electric and Magnetic Circuits, Rinehart Press, San Francisco, pp. 31–34, 1971):

$$W = \Delta t \Sigma P_i. \quad (1)$$

In the above equation, $\Delta t$ represents the constant intervals (in seconds) in which microwave power is measured and the summation $\Sigma$ is over the complete treatment interval with the power (in Watts) in the ith interval denoted by $P_i$.

The microwave energy W has units of watt-seconds, which is also designated as Joules. For example, in three consecutive 60-second intervals if the microwave power is 30 watts, 50 watts, 60 watts, respectively, the total microwave energy delivered in 180 seconds is calculated as W=60 (30 +50+60)=8,400 watt-seconds=8,400 Joules=8.4 kJ.

To understand better the focused energy per unit time W' (where ' denotes prime) deposited at a central position in homogeneous breast tissue of varying thickness (denoted by D) by dual-opposing applicators, consider the following calculation. Let $P_1$ and $P_2$ be the power delivered to the two applicators, respectively. The electric field radiated by each applicator is proportional to the square root of the power delivered to the applicator. Assuming symmetry, the radiated fields are in-phase at the central focused position from the two applicators. Assuming equal power from each applicator, that is, $P_1=P_2=P$, and plane wave illumination, then the focused energy per unit time at the central depth is expressed as $$W'(D) = |E|^2 = 4P \exp(-\alpha D). \quad (2)$$

Figure 7:
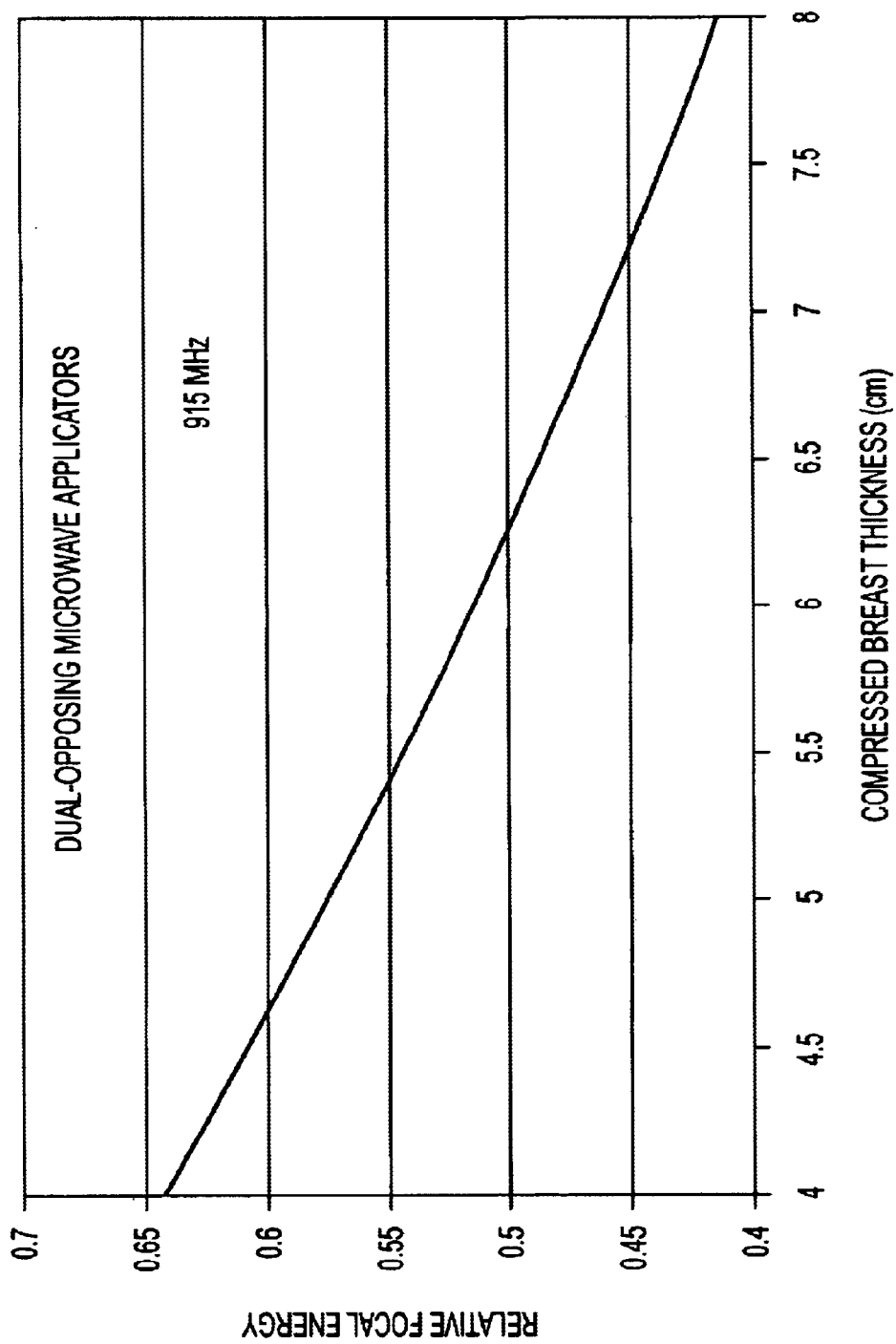
FIG. 7 shows the calculated focal microwave energy as a function of compressed breast tissue thickness.

Equation (2) was used to compute the focused 915 MHz energy per unit time at the central depth of normal breast tissue varying in thickness from 4 cm to 8 cm with the attenuation constant equal to 0.11 radians/cm, as shown in Table 4 and FIG. 7.

TABLE 4

Relative microwave energy at a central focus in simulated normal breast tissue for dual-opposing 915 MHz plane waves.

| Compression Thickness (cm) | Relative Energy at Focus |
|---|---|
| 4.00 | 0.643 |
| 4.25 | 0.626 |
| 4.50 | 0.608 |
| 4.75 | 0.592 |
| 5.00 | 0.576 |
| 5.25 | 0.560 |
| 5.50 | 0.545 |
| 5.75 | 0.530 |
| 6.00 | 0.516 |
| 6.25 | 0.502 |
| 6.50 | 0.488 |
| 6.75 | 0.475 |
| 7.00 | 0.462 |
| 7.25 | 0.449 |
| 7.50 | 0.437 |

TABLE 4-continued

Relative microwave energy at a central focus in simulated
normal breast tissue for dual-opposing 915 MHz plane waves.

| Compression Thickness (cm) | Relative Energy at Focus |
|---|---|
| 7.75 | 0.425 |
| 8.00 | 0.413 |

For a given power level, higher energy occurs at the focus as the focal position moves towards the skin.

Calculation of Equivalent Thermal Dose

The cumulative or total equivalent thermal dose relative to 43 degrees Celsius is calculated as a summation (Sapareto, et al., International Journal of Radiation Oncology Biology Physics, Vol. 10, pp. 787–800, 1984):

$$t_{43° C.} \text{ equivalent minutes}=\Delta t \Sigma R^{(43-T)}, \quad (3)$$

where $\Sigma$ is the summation over a series of temperature measurements during the treatment, T is the series of temperature measurements ($T_1, T_2, T_3, \ldots$), $\Delta t$ is the constant interval of time (units of seconds and converted to minutes) between measurements, R is equal to 0.5 if T>43° C. and R is equal to 0.25 if T<43° C. The equivalent thermal dose calculation is useful for assessing any possible heat damage to the breast tissues and skin.

Detailed Microwave Specific Absorption Rate Calculations in Simulated Breast Tissue To estimate the heating pattern in normal breast tissue and in normal breast tissue with tumor exposed to microwave radiation, three-dimensional specific absorption rate (SAR) heating patterns were calculated using finite-difference time-domain theory and computer simulations (Taflove, Computational Electrodynamics: The finite-difference time-domain method, Artech House, Inc., Norwood, Mass., p. 642, 1995). As depicted in FIG. 7, these simulations were performed by modeling dual-opposing TEM-2 waveguide applicators (Celsion Corp., Columbia, Md.) operating at 915 MHz. The applicators were coherently combined to focus the radiated beam at the central position in 6 cm thick homogeneous normal (mixture of fat and glandular) breast tissue. The applicators are assumed to radiate through thin sheets of plexiglass that simulate the plates used for breast compression in the adaptive phased array breast hyperthermia system.

Figure 8:
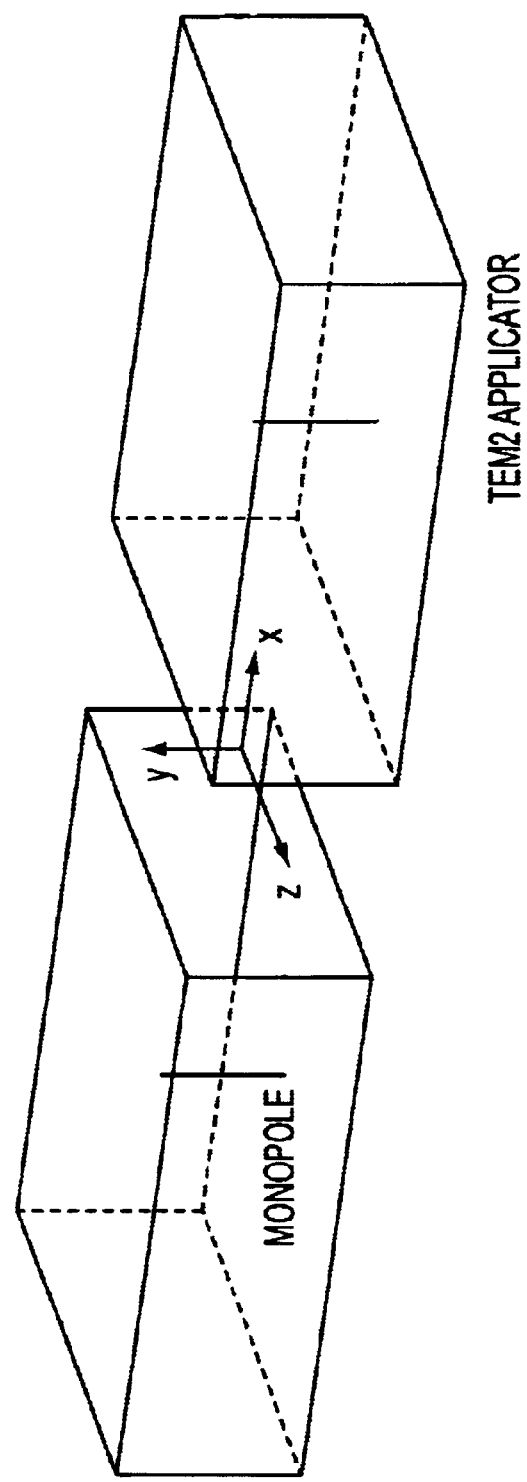
FIG. 8 shows a three-dimensional view of the computer simulated dual-opposing microwave waveguide applicators used in heating the breast.

Each metallic waveguide is loaded on the side walls with high dielectric constant material, which is used to match and shape the radiation inside the waveguide aperture. The waveguide applicators are linearly polarized with the alignment of the E-field in the y direction as in FIG. 8. A flat sheet of 3 mm thick plexiglass is adjacent to each applicator and parallel to the waveguide aperture. Between the two opposing TEM-2 applicators is a 6 cm thick homogeneous normal breast tissue phantom. The remaining volume is filled with cubic cells that model air.

The SAR distributions were calculated by squaring the electric field amplitude and multiplying by the electrical conductivity of the tissue. SAR is often described in levels (50% is usually designated as the effective heating zone) relative to the maximum SAR value of 100%. The SAR is proportional to the initial rise in temperature per unit time ignoring blood flow and thermal conduction effects.

Figure 9:
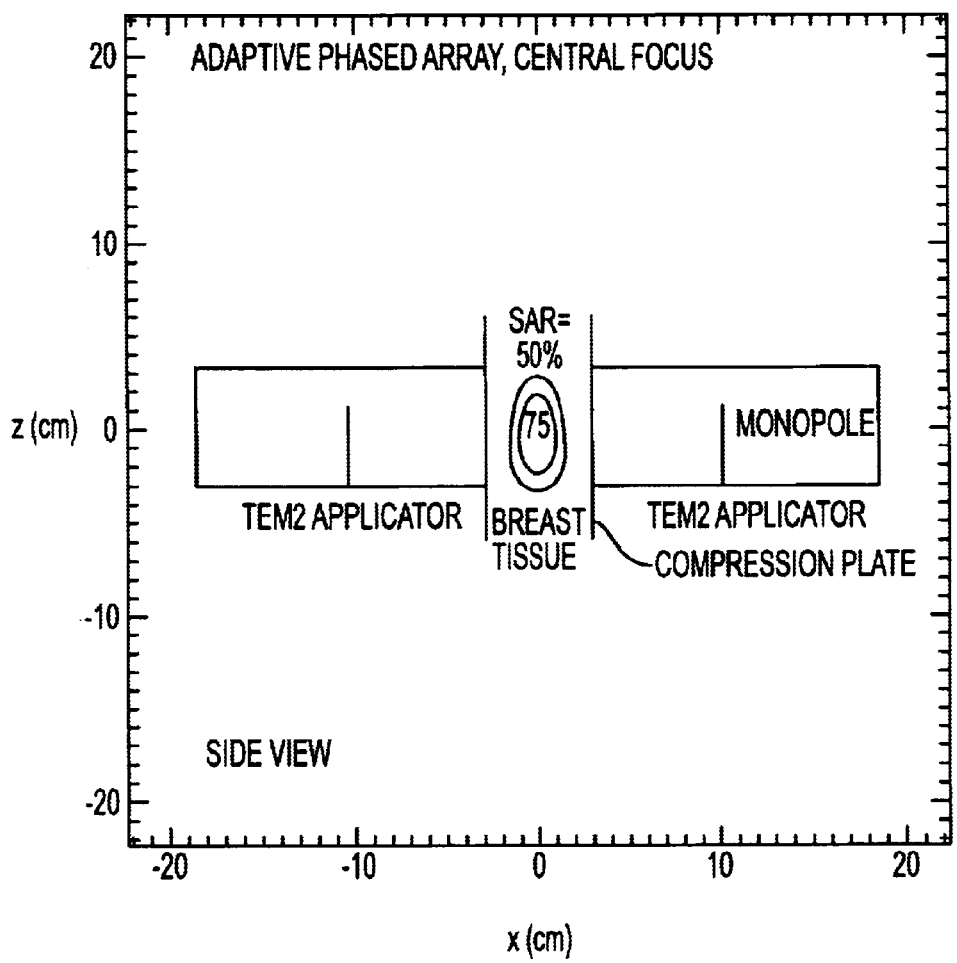
FIG. 9 shows a calculated side view of the 915 MHz specific absorption rate (SAR) heating pattern in homogeneous normal breast tissue with central focus.
Figure 10:
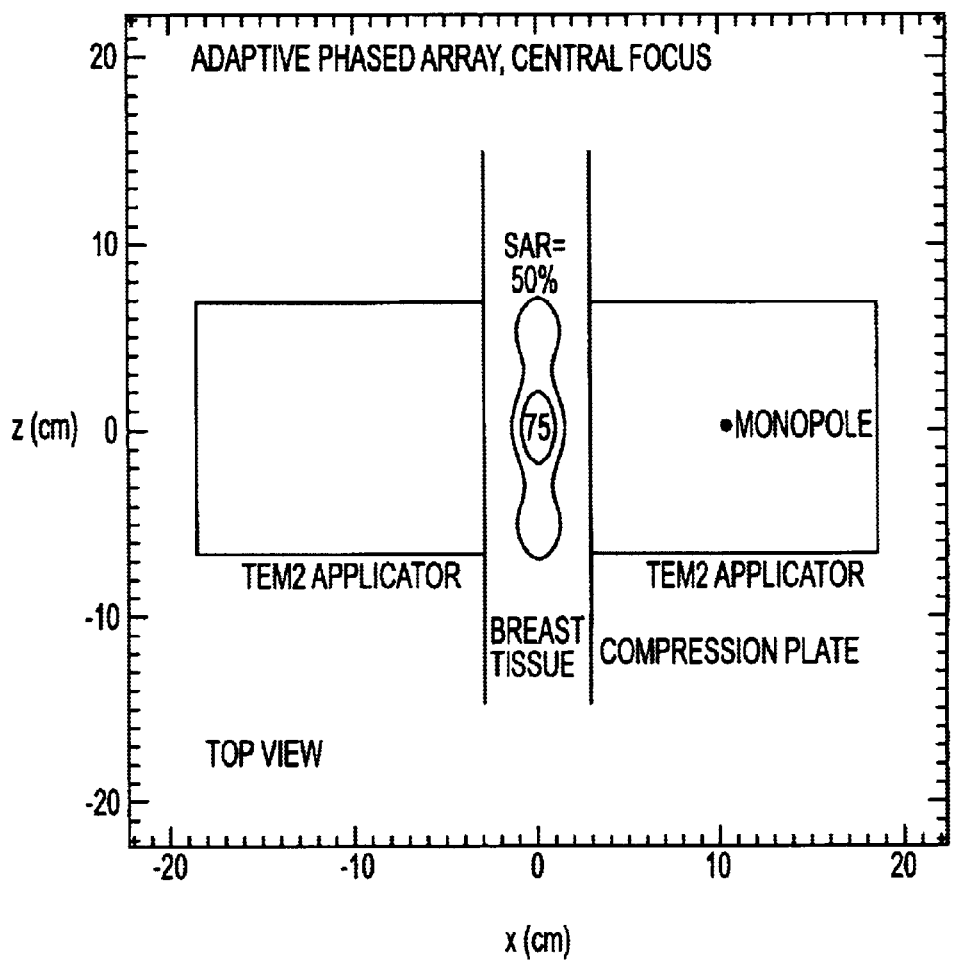
FIG. 10 shows a calculated top view of the 915 MHz SAR heating pattern in homogeneous normal breast tissue with central focus.
Figure 11:
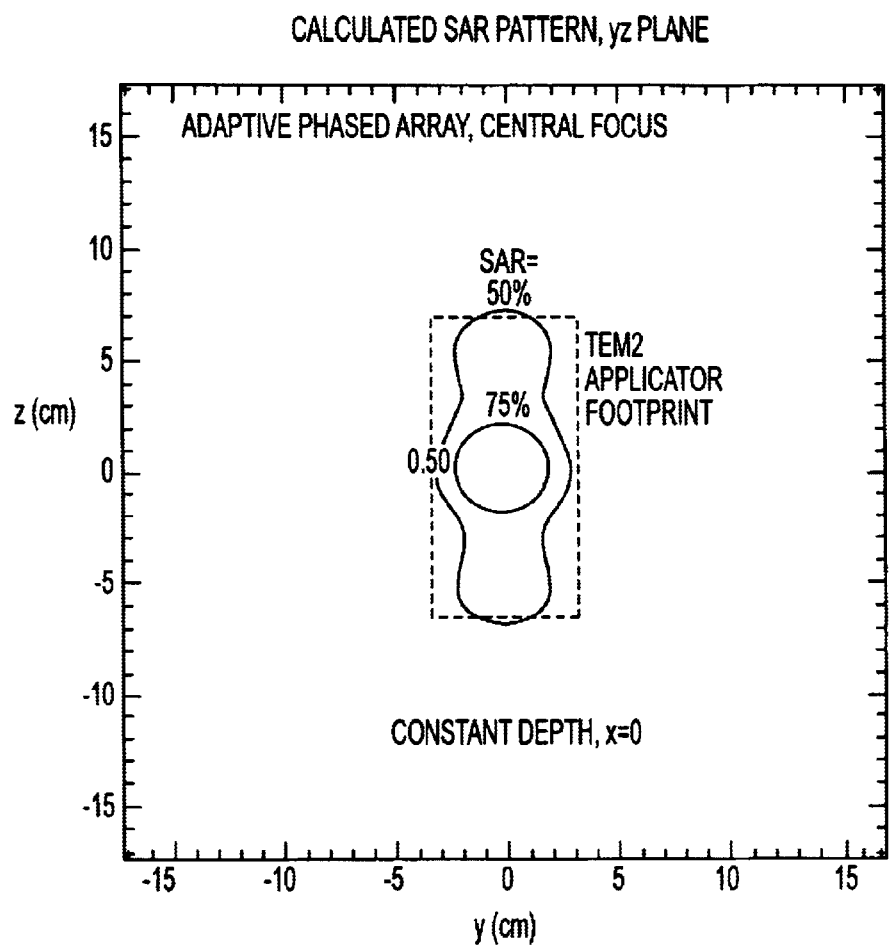
FIG. 11 shows a calculated end view of the 915 MHz SAR heating pattern in homogeneous normal breast tissue with central focus.

The SAR patterns were computed in the three principal planes (xy, xz, yz) as shown in FIGS. 9 to 13 for homogeneous normal breast tissue. The SAR side view (xy plane, z=0) pattern (75% and 50% contours) in homogenous normal breast tissue is shown in FIG. 9. The pattern generally is bell shaped and centered between the TEM-2 applicators. FIG. 10 shows the top view (xz plane, y=0) SAR pattern (75% and 50% contours). The pattern exhibits a small elliptically shaped 75% SAR region surrounded by a three-lobe shaped elliptical 50% SAR region. The small size of the 75% SAR is due to the mode shape of the radiated electric field for this type of applicator. FIG. 11 shows the end view (yz plane, x=0) of the SAR pattern (75% and 50% contours). The pattern exhibits a small circularly shaped 75% SAR region surrounded by a three-lobe shaped elliptical 50% SAR region approximately the size of the waveguide aperture.

Figure 12:
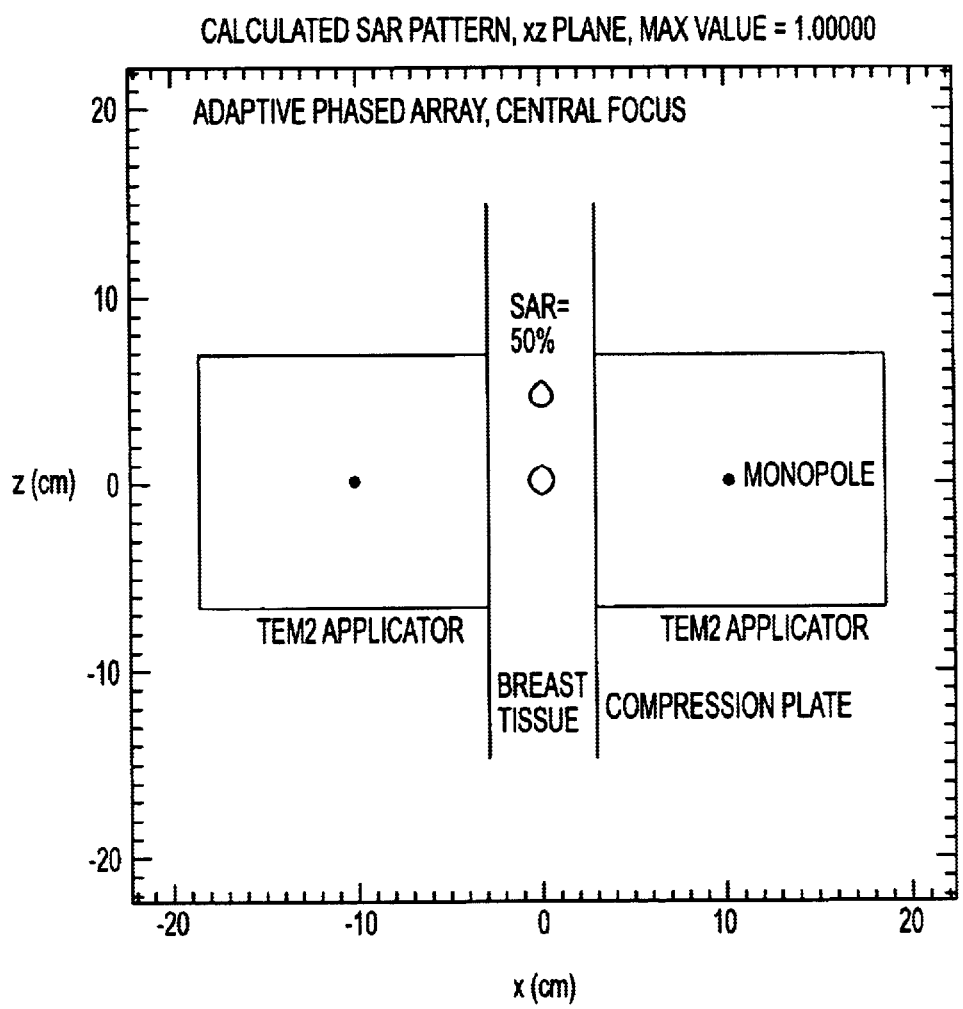
FIG. 12 shows a calculated top view of the 915 MHz SAR heating pattern when there are two simulated breast tumors, each with a diameter of 1.5 cm, spaced 5 cm apart. The 50% SAR contours are aligned with the tumors indicative of selective heating.
Figure 13:
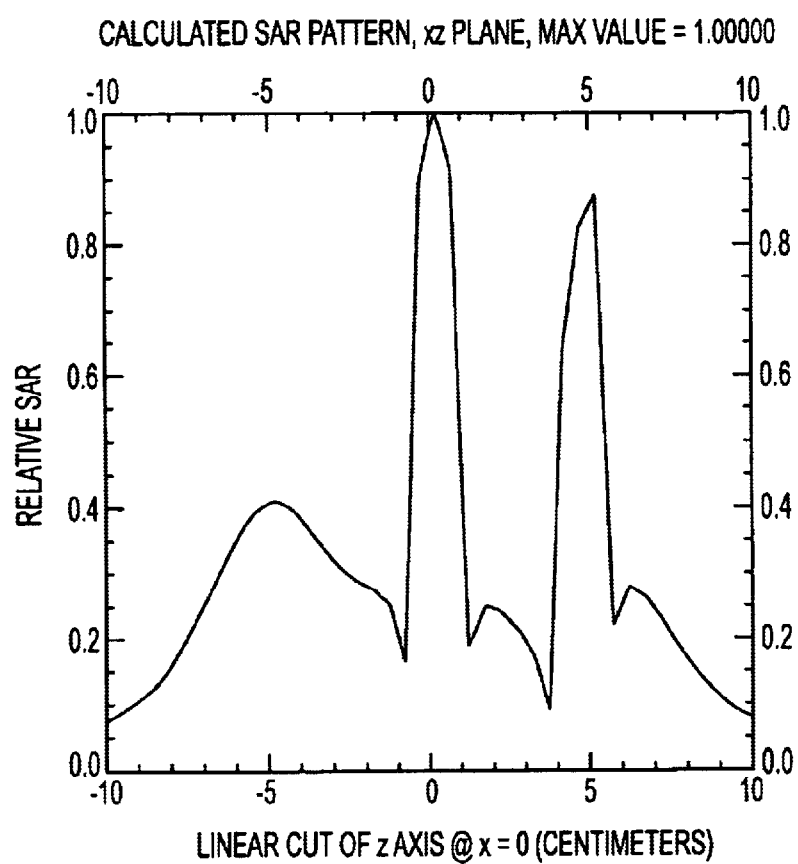
FIG. 13 shows a calculated linear cut of the 915 MHz SAR heating pattern (through the central plane of FIG. 12) when there are two simulated breast tumors, each with a diameter of 1.5 cm, spaced 5 cm apart. The SAR has sharp peaks that are aligned with the tumors indicative of selective heating.

The results shown in FIGS. 9 to 11 show that a large volume of deep breast tissues can be heated by the adaptive phased array with TEM-2 waveguide applicators, whereas the superficial tissues are not substantially heated. Any high-water content tissues exposed to this large heating field will be preferentially heated compared to the surrounding normal breast tissue. To demonstrate selective (preferential) heating, two spherically shaped 1.5-cm diameter simulated tumors (dielectric constant 58.6, electrical conductivity 1.05 S/m) were embedded in the normal breast tissue with 5-cm spacing and the FDTD calculation for the top view is shown in FIG. 12. Comparing this result with FIG. 10, it is clear that the SAR pattern has changed significantly and the two high-water content tumor regions are selectively heated. To show the sharpness of the selective heating, the calculated SAR pattern along the z axis at x=0 cm is shown in FIG. 13. There is a sharp peak located at the positions of the two tumors, again demonstrating selective heating of high-water content carcinoma compared to the surrounding normal breast tissue. Similar results would be expected for benign breast lesions such as fibroadenomas and cysts.

Figure 14:
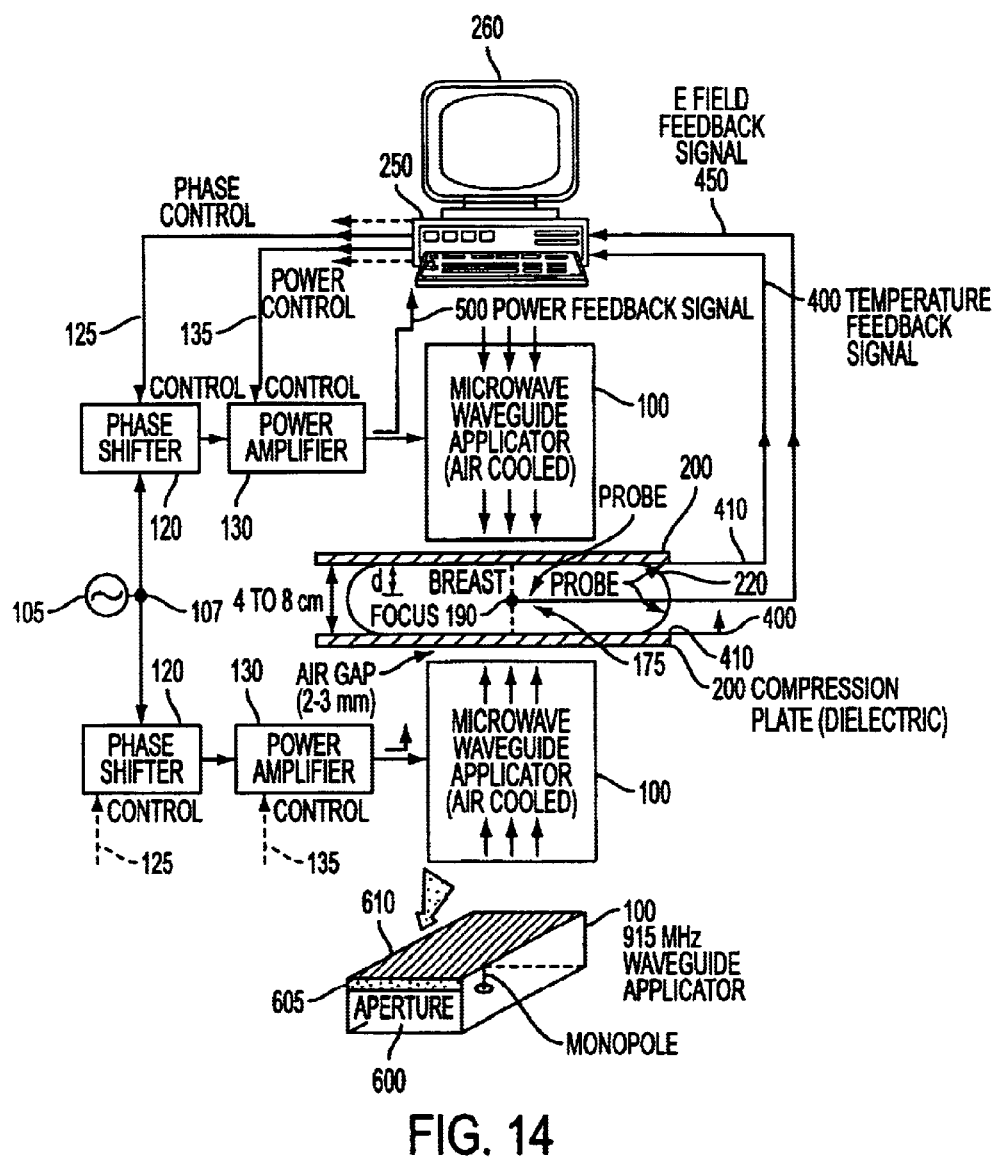
FIG. 14 illustrates a breast thermotherapy system according to the invention with added safety features including microwave absorbing pad on top of waveguide applicator and metallic shield covering top section of waveguide aperture.

FIG. 14 shows the externally focused adaptive phased array thermotherapy system od FIG. 5 with two of the safety methods applied to the waveguide applicators 100. In the preferred embodiment, a thin metallic shielding strip 605 of width 1 to 2 cm covers the top section of the rectangular waveguide aperture 600 to block stray radiation from reaching the base of the breast near the chest wall region. A thin microwave absorbing pad 610 (for example, 0.125-inch thick Cuming Microwave Corporation MT-30 sheet absorber, attenuation 40 dB/inch) covers the entire top surface of the waveguide applicator 100 (for example, Celsion Corporation TEM2 waveguide applicator). The microwave absorbing pad 610 can attenuate or suppress any microwave surface currents that could reradiate microwave energy toward the base of the breast and chest wall region. The microwave-absorbing pad 610 is glued or otherwise attached to the top surface of the waveguide applicator.

Figure 15:
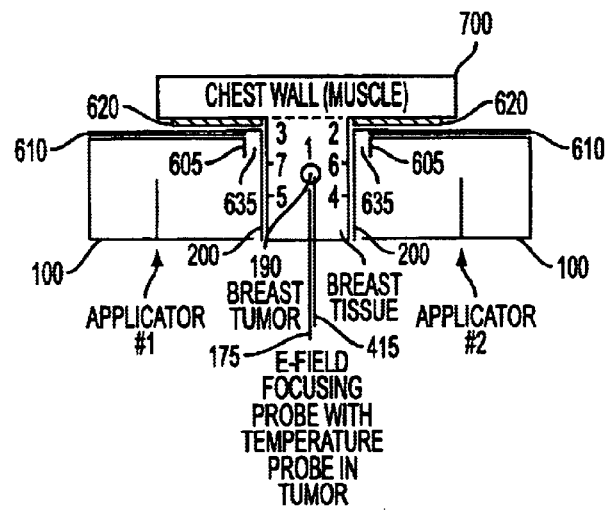
FIG. 15 is a side view showing a simple T-shaped breast phantom with microwave absorbing pads, metallic shielding, air gaps, and combined E-field focusing and temperature probes.

FIG. 15 shows a side view of the externally focused adaptive phased array thermotherapy applicators 100 with breast compression plates (paddles) 200 on either side of a simple T-shaped breast phantom 700 that is used to simulate the breast for microwave heating experiments. The applicators 100 have pads 610 and microwave shielding strip 605 with additional insulating pads 620 placed between compression plate 200 and the phantom T 700 representing the chest wall or muscle supporting the breast tissue. A T-shaped phantom enclosure is fabricated preferably from plexiglass or other plastic material and is part of compression plates 200. In a preferred embodiment, the upper "T" section of compression plates 200 extends between pad 610 and pad 620 for a distance, as shown in FIG. 15. The upper section of the T-shaped breast phantom 700 contains muscle equivalent phantom tissue (M. Gauthrie, editor: Methods of External Hyperthermic Heating, Springer Verlag, p. 11 (Chou formulation), 1990) and the lower section contains fatty dough breast equivalent phantom tissue (J. J. W. Lagendijk and P. Nilsson, "Hyperthermia Dough: A Fat and Bone Equivalent Phantom to Test Microwave/Radiofrequency Hyperthermia Heating Systems," Physics in Medicine and Biology, Vol. 30, No. 7, pp. 709–712, 1985). Pad 620 is soft for comfort and contains microwave-absorbing material to reduce stray microwave energy.

Applicators 100 are designed so that a gap region 635 is provided between the applicator and the breast tissue. Gap region 635 allows airflow from external air tubes or fans that are pointed into the gap to cool the region in proximity to the base of each side of the breast and chest wall region. In a preferred embodiment, plastic air tubes with flared or conical shaped nozzles, such as those manufactured by Lockwood Products, Inc., Lake Oswego, Oreg. may be used to guide airflow into gap region 635 to cool the breast region.

In a preferred embodiment, a fiber optic temperature sensor probe 415 and an E-field microwave-focusing probe 175 are parallel to one another and co-located within a single catheter. The tip of the fiber optic temperature sensor is positioned within the tumor site or focus position 190 and the E-field focusing probe 175 is located at the same depth of the tumor as measured between the compression plates. The fiber optic temperature sensor in the tumor can be of the fluroptic type is non-metallic and does not interfere with the microwave energy (M. Gauthrie, editor: Methods of External Hyperthermic Heating, Springer Verlag, p. 119, 1990). The metallic E-field focusing probe 175 consists of very thin metallic coaxial cable 0.020 inches diameter (UT-20). The tip section of the E-field focusing probe 175 consists of the center pin of the coaxial cable extending approximately 1 cm beyond the outer jacket of the coaxial cable. The tip of the E-field focusing probe is positioned approximately 0.5 cm from the tip of the fiber optic temperature sensor.

Figure 16:
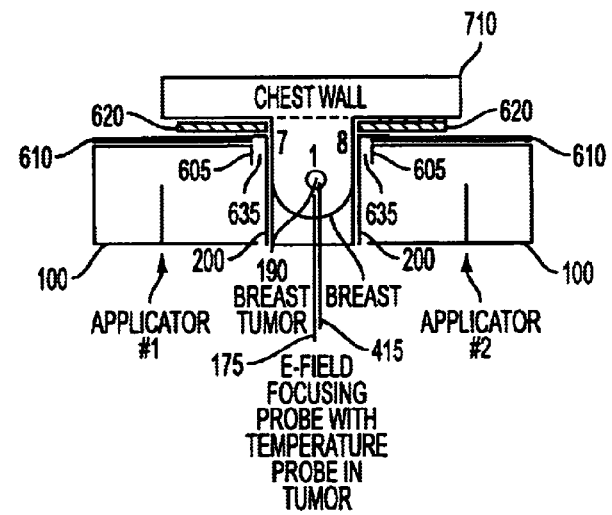
FIG. 16 is a side view showing a breast-shaped phantom with microwave absorbing pads, metallic shielding, air gaps, and combined E-field focusing and temperature probes.

FIG. 16 shows a more realistically shaped breast phantom 710 in which the breast is curved. For this phantom, the curved breast portion can be fabricated using a plastic bag (polyethylene) filled with a compressible fat phantom material conforming to the shape of a breast. Compressible ultrasound breast imaging phantoms can also be used for microwave experiments. In FIG. 16, the positions labeled 7 and 8 are on the skin surface close to the base of the breast near the chest wall region. Further, as this diagram illustrates, a portion (lower portion below the skin entry point) of the metallic coaxial E-field focusing probe 175 is not shielded by the breast tissue and is directly exposed to the microwave energy radiated by the two waveguide applicators 100. The microwave energy can possibly overheat the exposed metallic coaxial cable resulting in a skin burn where the E-field focusing probe enters the skin. In such a case, it is desirable to remove the E-field focusing probe 175 after the microwave focusing procedure is completed prior to heating the breast. The preferred E-field focusing probe 175 is a coaxial cable with the center pin extended to form a monopole antenna. However, the focusing probe can also be fabricated using a monopole or dipole antenna connected to parallel transmission lines of either metallic or carbon material. Alternatively, the focusing probe can be a monopole or dipole antenna with a microwave to optical converter connected to a fiber optic cable to avoid metallic heating effects at the skin entry point. The optical modulator may be a Mach Zehnder modulator, for example.

Figure 17:
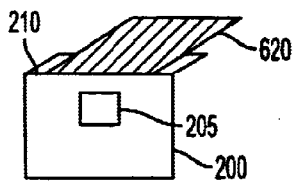
FIG. 17 shows a compression paddle with a rectangular shaped window in the vertical surface and a microwave absorbing pad attached to the top surface of the paddle.
Figure 18:
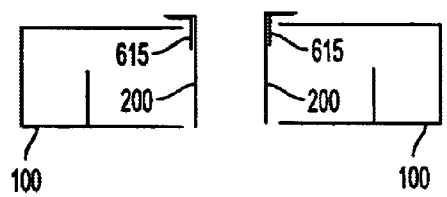
FIG. 18 is a side view of waveguide applicators with metallic shielding added to the upper portion of the compression paddles on the surface facing away from the breast skin.

FIG. 17 shows a detailed three-dimensional view of the improved safety method with compression plate 200 and pad 620. The compression plate edge 210 is a potential source for damage to the skin as a right angle is formed by the vertical and horizontal surfaces of the plate and the edge is adjacent the chest wall and breast tissue. Accordingly, microwave-absorbing pad 620 is disposed between edge 210 and the chest wall. The microwave-absorbing pad 620 serves two purposes. First, the pad contains a soft foam material and cushions the breast skin from abrasion or pressure as the breast is compressed against the compression plate edge 210. Second, the pad contains microwave-absorbing material to attenuate any stray microwave radiation from the applicators 100 that might overheat nearby tissue. The compression plate 200 or paddle may contain one or more rectangular openings 205 to allow an ultrasound transducer to touch the skin for imaging the breast tissue while the E-field focusing probe and temperature probe are inserted in the breast tumor region. In another embodiment according to the invention, FIG. 18 shows a side view of the waveguide applicators 100 and compression plates 200 with metallic shielding strips 615 glued or otherwise attached to the surface of the compression plates 200 facing away from the breast skin.

Shielding Experiment Results

As discussed above, FIG. 15 shows the geometry of externally focused adaptive phased array microwave thermotherapy for breast tumor treatment. In testing, two Celsion Corporation TEM-2 microwave applicators radiating at 915 MHz were used to induce thermotherapy. For simplicity, the patient tissue is represented by a phantom consisting of a T-shaped plexiglass box containing simulated breast tissue in the lower portion and simulated muscle tissue in the upper portion. Additionally, a simulated breast tumor consisting of muscle phantom tissue (approximately 1.5 cm diameter) was located at position 1. Seven temperature probes (designated #1 to #7) were used in these experiments. Probe 1 was a fiberoptic temperature probe and the remaining probes were thermocouple probes that rest outside the simulated skin of the breast tissue. Probe 1 was positioned at the desired focus site 190 where the simulated tumor position is located. Probes 2 and 3 were located at the top corner of the compression paddles outside of the primary microwave field. Probes 4 and 5 were located in the center of the microwave field where the maximum field strength exists. Probes 6 and 7 were located above probes 4 and 5 where a lower field strength would be expected. An E-field focusing probe 175 was also placed at the same depth as Probe position 1 to focus the microwave energy. The E-field focusing probe 175 and fiber optic temperature probe 1 were inserted within a common catheter (Teflon, 1.65 mm outer diameter).

Two experiments were conducted in which the microwave power to each channel was 70 Watts and the phase shifters in the array were adaptively focused to central probe position #1 in a 6 cm thick breast phantom. In the first experiment, no microwave absorbers or metallic shielding was used, as shown in FIG. 5. In the second experiment, microwave absorbing pads and a metallic strip shield covering the top portion (2 cm) of the aperture was used as depicted in FIG. 15. In each experiment, the initial temperature slope (degrees per minute) for each measurement sensor was calculated for the first 30-seconds of heating.

TABLE 5

Measured temperature slopes for no absorber and no shielding.

| Temperature Sensor | Temperature Slope (no absorber, no shielding) |
| --- | --- |
| 1 (simulated tumor position) | 3.8 deg C./minute |
| 2 (chest wall surface site, left) | 4.4 deg C./minute |
| 3 (chest wall surface site, right) | 5.2 deg C./minute |
| 4 (left skin surface, center of field) | 0.8 deg C./minute |
| 5 (right skin surface, center of field) | 1.0 deg C./minute |
| 6 (left skin surface, above center of field) | 0.8 deg C./minute |
| 7 (right skin surface, above center of field) | 1.6 deg C./minute |

Figure 19:
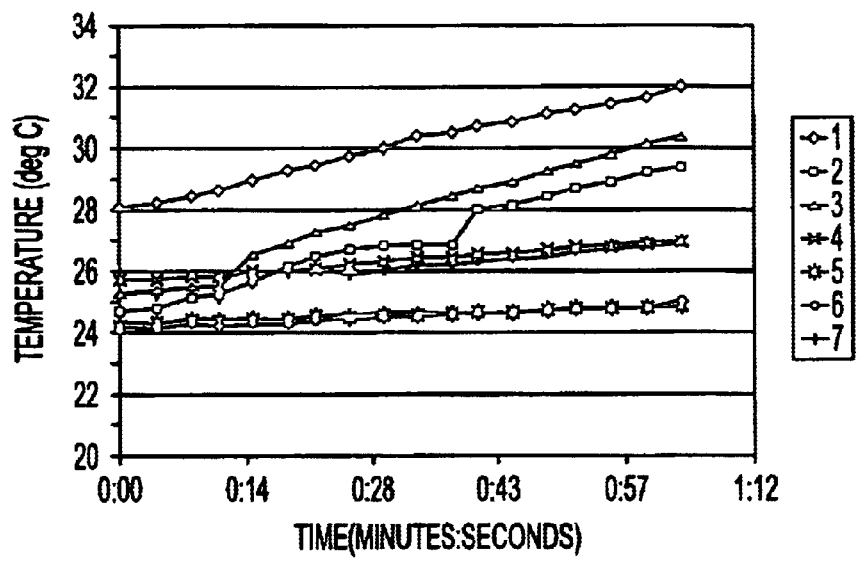
FIG. 19 is a graph showing measured temperature versus time for the simple T-shaped phantom heated by the adaptive phased array applicators, without shielding and absorbing pads.

The chest wall surface sites heat faster than the simulated tumor position. This is graphically shown in FIG. 19.

TABLE 6

Measured temperature slopes with absorber on top of the breast compression plate and on top of waveguide applicator and shielding covering the top section of the applicators.

| Temperature Sensor | Temperature Slope (with absorber and shielding) |
| --- | --- |
| 1 (simulated tumor position) | 5.6 deg C./minute |
| 2 (chest wall surface site, left) | 1.8 deg C./minute |
| 3 (chest wall surface site, right) | 2.4 deg C./minute |
| 4 (left skin surface, center of field) | 2.2 deg C./minute |
| 5 (right skin surface, center of field) | 1.6 deg C./minute |
| 6 (left skin surface, above center of field) | 0.8 deg C./minute |
| 7 (right skin surface, above center of field) | 1.2 deg C./minute |

Figure 20:
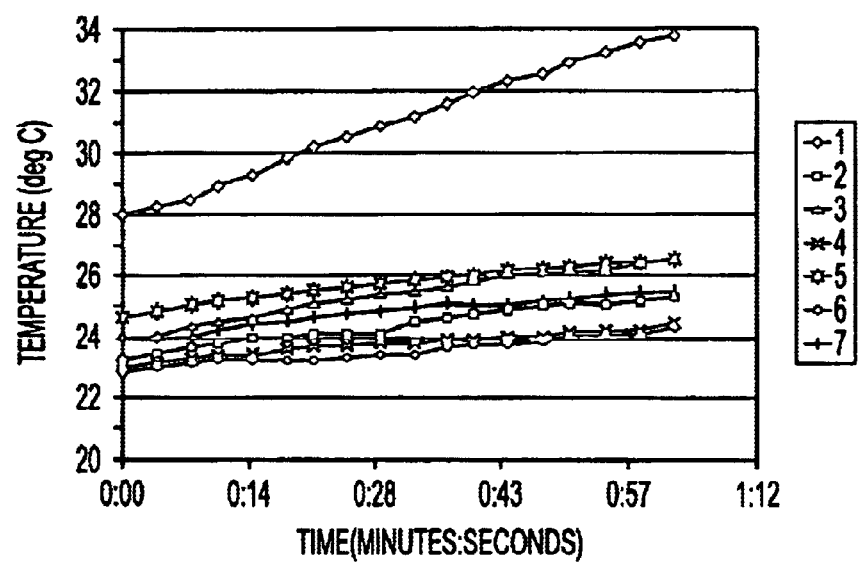
FIG. 20 is a graph showing measured temperature versus time as the simple T-shaped phantom heated by the adaptive phased array applicators with shielding and absorbing pads.

As the results in Table 6 show the simulated tumor site heats significantly faster than the surface sites including that of the chest wall region. This is illustrated graphically in FIG. 20. Accordingly, with the safety improvements, the tumor heated more rapidly and the temperature slopes for sensor positions 2 and 3 are one half those when the safety improvements are not used. The thermal results for these two experiments clearly show the effectiveness of the microwave absorber pads and metallic shielding strip covering the top section of the waveguide applicator in reducing the surface heating near the chest wall. The temperature slopes for sensor positions 4 and 5 increased with the safety improvements, but were still at least a factor of two lower than the tumor temperature slope. Additional airflow and cooled air could help to further reduce the surface heating.

In addition to the above-described microwave embodiment, applicants envision that other embodiments may employ any type of focused energy including electromagnetic, ultrasound, radio frequency, laser or other focused energy source that is known to those skilled in the art. That is, any energy or combination of different energies that can be focused to heat and ablate an area of tissue may be employed in the method according to Applicants' invention. While the focused energy may be the primary heating source, it may be combined with an injection of substance that increases or enhances heating at the target area (tumor). The substance may be saline water or water mixed with a metal or other electrical conducting substance, such as a metallic surgical breast clip so that the substance enhances the amount of heat delivered to the target area.

Since the injected substance enhances heating of the target area, this is an alternative method of obtaining selective heating of the target area. Consequently, Applicants envision that non-focused energy when combined with an injection of saline water or water mixed with metal would sufficiently heat the targeted area to ablate cancerous cells and/or benign cells. Thus, the energy applicator employed in this embodiment could be an applicator that delivers non-focused energy. In such an embodiment using only non-focused energy according to the invention, an E-field probe would not be necessary.

While this invention has been particularly shown and described with reference to preferred embodiments thereof, it will be understood by those skilled in the art that various changes in form and details may be made therein without departing from the spirit and scope of the invention as defined by the appended claims. For instance, although the hyperthermia system described herein is with respect to the treatment of breast carcinomas and benign breast lesions, the invention is applicable to the treatment of other types of cancers such as prostate, liver, lung, and ovarian as well as benign disease such as benign prostatic hyperplasia (BPH). Similarly, it is understood that the safety methods disclosed here can be applied to microwave or radiofrequency thermotherapy treatments of other appendages and portions of the human body such as legs and arms and the torso.

It is also understood that larger or smaller numbers of array antenna applicators, or a single antenna applicator, may be used with similar results. Furthermore, the methods disclosed here can be used with non-coherent multiple-applicator treatment systems—in a non-coherent system, a field focusing probe would not be necessary. In situations where compression of the breast or other organ is not desired or appropriate, the compression step can be omitted. If the compression step is not used, then the absorbing pads and other metallic shielding features may not be employed. Some of the methods and techniques described herein are also applicable to ultrasound hyperthermia system particularly the use of energy dose for feedback control. The method can be used to enhance radiation therapy or for targeted drug delivery using thermosensitive liposomes and/or targeted gene delivery. The invention is also applicable to non-medical hyperthermia systems, such as those used for heating of industrial or food materials.

We claim:

1. A method for treating cancerous or benign conditions of an organ by selective irradiation of the organ tissue with focused energy, the method comprising the steps of:
   a) Inserting an E-field probe sensor to an appropriate depth in the organ tissue;
   b) Monitoring temperatures of the skin surface adjacent the organ;
   c) Positioning two or more energy applicators around the organ;
   d) Setting the initial power level delivered to each energy applicator;
   e) Setting the initial relative phase delivered to each energy applicator to focus the energy at the E-field probe positioned in the organ tissue;
   f) Delivering energy to the two or more energy applicators to selectively irradiate the organ tissue with focused energy and treat at least one of cancerous and benign conditions of the organ;
   g) Adjusting the level of power to be delivered to each energy applicator during treatment based on the monitored skin temperatures;
   h) Monitoring the energy delivered to the energy applicators;
   i) Determining total energy delivered to the energy applicators and displaying the total energy in real time during the treatment; and
   j) Completing the treatment when the desired total energy dose has been delivered by the energy applicators to the organ.

2. The method of claim 1, wherein the focused energy is at least one of electromagnetic, ultrasound, radio frequency, and laser waves.

3. The method of claim 1, wherein the desired total energy dose delivered by the energy applicators to the organ is from approximately 25 kilojoules to approximately 500 kilojoules.

4. The method of claim 1, wherein the desired total energy dose delivered by the energy applicators to the organ is from approximately 200 kilojoules to approximately 500 kilojoules.

5. The method of claim 1, wherein for a heat alone treatment the energy applicators produce equivalent thermal doses up to approximately 400 minutes with peak tumor temperatures up to approximately 55 degrees C.

6. The method of claim 1, further comprising at least one of chemotherapy treatment and thermosensitive liposome treatment in combination with a heat treatment achieved by steps a)–j), wherein for combination heat and chemotherapy treatment or heat and thermosensitive liposome treatment, the energy applicators produce equivalent thermal doses of approximately 50 to 100 minutes with peak tumor temperatures up to approximately 46 degrees C.

7. The method of claim 1, wherein the organ is the breast and the energy dose delivered to the breast is between approximately 200 and 400 kilojoules.

8. A method for treating cancerous or benign conditions of the breast by selective irradiation of the breast tissue with focused energy, the method comprising the steps of:
  a) Compressing the breast between two compression plates;
  b) Applying an E-field probe sensor to one of an appropriate depth in the breast tissue and on the breast skin surface;
  c) Monitoring temperatures of the breast skin surface;
  d) Positioning two or more energy applicators around the compressed breast thereby surrounding the breast in a ring;
  e) Delivering focused energy to the two or more energy applicators to selectively irradiate the breast tissue with focused energy and treat at least one of cancerous and benign conditions of the breast; and
  f) Adjusting the power to be delivered to each energy applicator during treatment based on the monitored skin temperatures.

9. The method for treating cancerous or benign conditions of the breast according to claim 8, wherein the focused energy is microwave energy and further comprising the step of maintaining the compression of the breast following the application of microwave energy to the breast tissue in order to accumulate added thermal dose in the treated breast tissue while the breast skin surface temperature is cooled.

10. The method for treating cancerous or benign conditions of the breast according to claim 8, wherein one of chemotherapy, gene therapy including gene based modifiers, thermosensitive liposomes containing chemotherapy, and radiation therapy is used in conjunction with selective irradiation of the breast tissue with focused energy.

11. The method for treating cancerous or benign conditions of the breast according to claim 8, further comprising the step of administering Adriamycin (Doxorubicin) and Cytoxan (Cyclophosphamide) for four cycles, wherein steps a)–f) are conducted for up to three cycles within approximately 36 hours from the time a cycle of Adriamycin/Cytoxan is administered.

12. The method for treating cancerous or benign conditions of the breast according to claim 11, wherein approximately 60 mg/m$^2$ of Adriamycin (Doxorubicin) and approximately 600 mg/m$^2$ of Cytoxan (Cyclophosphamide) is administered each cycle and approximately 21 days elapse between each cycle.

13. The method for treating cancerous or benign conditions of the breast according to claim 8, further comprising the step of administering up to four cycles of Adriamycin (Doxorubicin) at approximately 60 mg/m$^2$ and Cytoxan (Cyclophosphamide) at approximately 600 mg/m$^2$ where each cycle is administered approximately every 21 days; and
  wherein steps a)–f) is one cycle of thermotherapy treatment and at least one thermotherapy treatment is administered after the first cycle of Adriamycin/Cytoxan is completed or approximately 21 days after the first cycle of Adriamycin/Cytoxan is infused into the blood stream of a patient.

14. The method for treating cancerous or benign conditions of the breast according to claim 8, wherein steps a)–f) is one cycle of thermotherapy treatment and thermotherapy is used in combination with at least one of chemotherapy, radiation therapy and gene-based modifiers therapy following a lumpectomy to treat residual ductal carcinoma in-situ.

15. The method for treating cancerous or benign conditions of the breast according to claim 8, wherein steps a)–f) is one cycle of thermotherapy treatment and the thermotherapy treatment is used following a lumpectomy to treat residual ductal carcinoma in-situ.

16. The method for treating cancerous or benign conditions of the breast according to claim 8, wherein steps a)–f) is one cycle of thermotherapy treatment and a cycle of thermotherapy is applied prior to an incision to remove cancerous or benign conditions of the breast so that margins surrounding the cancerous or benign conditions that is to be removed surgically are treated pre-surgery to reduce the amount of at least one of cancerous cells, mutant cells and abnormal cells in the margins and thus the rate of additional incisions.

17. The method for treating cancerous or benign conditions of the breast according to claim 16, wherein thermosensitive liposome treatment is used in combination with the thermotherapy treatment to enhance the destruction of at least one of cancerous cells, mutant cells and abnormal cells in the margins.

18. The method for treating cancerous or benign conditions of the breast according to claim 8, further comprising the step of administering one of Doxorubicin and Docetaxel, and FAC (5-Fluorouracil, Doxorubicin, and cyclophosphamide) in combination with up to four cycles of thermotherapy treatment, wherein steps a)–f) is one cycle of thermotherapy treatment.

19. The method for treating cancerous or benign conditions of the breast according to claim 8, wherein steps a)–f) is one cycle of thermotherapy treatment and the thermotherapy treatment alone is used as treatment for early stages of breast cancer.

20. A method for preventing breast cancer by combining the thermotherapy treatment defined by steps a)–f) of claim 8 with a drug to block estrogen from binding with estrogen receptors, wherein the thermotherapy treatment is performed at approximate one-year intervals over 5 years in combination with a drug that blocks estrogen from binding with estrogen receptors of breast carcinomas, by one of blocking or modifying the estrogen receptors, and killing breast carcinomas directly with heat.

21. The method for preventing breast cancer according to claim 20, wherein the drug that blocks estrogen is Tamoxifen.

22. The method for preventing breast cancer according to claim 21, wherein the dose of Tamoxifen administered is approximately 20 mg per day for the five year period.

23. A method for treating cancerous or benign conditions of an organ by selective irradiation of the organ tissue with energy, the method comprising the steps of:
  a) Injecting a substance that enhances heating to an appropriate depth in the organ tissue;
  b) Monitoring temperatures of the skin surface adjacent the organ;
  c) Positioning at least one energy applicator about the organ;
  d) Setting the initial power level delivered to each at least one energy applicator;
  e) Delivering energy to the at least one energy applicator to selectively irradiate the organ tissue with energy and treat at least one of cancerous and benign conditions of the organ;
  f) Adjusting the level of power to be delivered to each at least one energy applicator during treatment based on the monitored skin temperatures;
  g) Monitoring the energy delivered to the at least one energy applicator;
  h) Determining total energy delivered to the at least one energy applicator and displaying the total energy in real time during the treatment; and
  i) Completing the treatment when the desired total energy dose has been delivered by the at least one energy applicator to the organ.

24. The method according to claim 23, wherein the substance is metal or one of saline water and water mixed with metal or other electrical conductor.

25. The method of claim 23, wherein the energy is at least one of electromagnetic, ultrasound, radio frequency, and laser waves.

* * * * *